(12) United States Patent
Venturino et al.

(10) Patent No.: US 8,147,472 B2
(45) Date of Patent: Apr. 3, 2012

(54) FOLDED ABSORBENT PRODUCT

(75) Inventors: Michael Barth Venturino, Appleton, WI (US); Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1861 days.

(21) Appl. No.: 10/721,829

(22) Filed: Nov. 24, 2003

(65) Prior Publication Data
US 2005/0113776 A1    May 26, 2005

(51) Int. Cl.
*A61F 13/15* (2006.01)
*A61F 13/20* (2006.01)

(52) U.S. Cl. .............................. 604/385.201

(58) Field of Classification Search ........... 604/385.01, 604/378–380, 385.201; 428/152
See application file for complete search history.

(56) References Cited

U.S. PATENT DOCUMENTS

| | | | |
|---|---|---|---|
| 2,852,026 A | 9/1958 | Karr | |
| 3,461,871 A | 8/1969 | Foote | |
| 3,559,648 A | 2/1971 | Mason, Jr. | |
| 3,693,621 A | 9/1972 | Jarusik et al. | |
| 3,739,783 A | 6/1973 | Broerman | |
| 3,765,418 A | 10/1973 | Jones, Sr. | |
| 3,766,922 A | 10/1973 | Krusko | |
| 3,769,978 A | 11/1973 | DeNight et al. | |
| 3,771,524 A | 11/1973 | Ralph | |
| 3,842,837 A | 10/1974 | Sward | |
| 3,860,002 A | 1/1975 | Kolbach | |
| 3,920,017 A | 11/1975 | Karami | |
| 3,963,022 A | 6/1976 | Rotello | |
| 4,022,456 A | 5/1977 | Hooper et al. | |
| 4,040,423 A | 8/1977 | Jones, Sr. | |
| 4,100,324 A | 7/1978 | Anderson et al. | |
| 4,265,245 A | 5/1981 | Glassman | |
| 4,381,782 A | 5/1983 | Mazurak et al. | |
| 4,388,056 A | 6/1983 | Lee et al. | |
| 4,410,324 A | 10/1983 | Sabee | |
| 4,425,127 A | 1/1984 | Suzuki et al. | |
| 4,501,587 A | 2/1985 | Enloe | |
| 4,519,800 A * | 5/1985 | Merry | 604/385.25 |
| 4,560,380 A | 12/1985 | Tharel | |
| 4,560,381 A | 12/1985 | Southwell | |

(Continued)

FOREIGN PATENT DOCUMENTS
EP    0432882 A2    6/1991
(Continued)

OTHER PUBLICATIONS

Translation of Japanese Patent No. JP60194947, 8 pages, Oct. 3, 1985.

(Continued)

*Primary Examiner* — Melanie Hand
(74) *Attorney, Agent, or Firm* — Dority & Manning, P.A.

(57) ABSTRACT

Absorbent structures are disclosed which may be incorporated into liquid absorbent products, such as diapers, adult incontinence products, feminine hygiene products, and the like. The absorbent structures are made from a fibrous material and include a pair of opposing lateral flaps. The lateral flaps are folded onto the fibrous web. By folding the lateral flaps onto the fibrous web, greater basis weight areas may be formed on the absorbent structure. By varying the width of the lateral flaps, the basis weight differential may be increased and decreased. The lateral flaps also form the widest portion of the web material for facilitating folding during a continuous process.

26 Claims, 19 Drawing Sheets

U.S. PATENT DOCUMENTS

| | | | |
|---|---|---|---|
| 4,585,448 A | 4/1986 | Enloe | |
| 4,615,695 A | 10/1986 | Cooper | |
| 4,626,184 A | 12/1986 | Hammond | |
| 4,640,810 A | 2/1987 | Laursen et al. | |
| 4,644,945 A | 2/1987 | Thorner | |
| 4,648,861 A | 3/1987 | Pierce | |
| 4,655,759 A | 4/1987 | Romans-Hess et al. | |
| 4,666,647 A | 5/1987 | Enloe et al. | |
| 4,670,011 A * | 6/1987 | Mesek | 604/378 |
| 4,670,111 A * | 6/1987 | Toomey, Jr. | 205/416 |
| 4,690,719 A * | 9/1987 | Lucas et al. | 156/201 |
| 4,704,116 A | 11/1987 | Enloe | |
| 4,741,941 A | 5/1988 | Englebert et al. | |
| 4,761,258 A | 8/1988 | Enloe | |
| 4,762,738 A | 8/1988 | Keyes et al. | |
| 4,795,453 A * | 1/1989 | Wolfe | 604/385.101 |
| 4,795,454 A | 1/1989 | Dragoo | |
| 4,830,187 A | 5/1989 | Keyes et al. | |
| 4,927,582 A | 5/1990 | Byrson | |
| 4,930,942 A | 6/1990 | Keyes et al. | |
| 4,940,464 A | 7/1990 | Van Gompel et al. | |
| 4,950,263 A | 8/1990 | Lewis | |
| 4,950,264 A | 8/1990 | Osborn, III | |
| 4,960,477 A * | 10/1990 | Mesek | 156/209 |
| 4,961,736 A | 10/1990 | McCloud | |
| 4,967,768 A | 11/1990 | Tatro | |
| 5,009,653 A | 4/1991 | Osborn, III | |
| 5,019,070 A | 5/1991 | Ruben | |
| 5,021,051 A | 6/1991 | Hiuke | |
| 5,055,103 A | 10/1991 | Nomura et al. | |
| 5,071,648 A | 12/1991 | Rosenblatt | |
| 5,087,253 A | 2/1992 | Cooper | |
| 5,090,424 A | 2/1992 | Simon et al. | |
| 5,091,998 A | 3/1992 | Witzke | |
| 5,104,116 A | 4/1992 | Pohjola | |
| 5,147,345 A | 9/1992 | Young et al. | |
| 5,147,347 A | 9/1992 | Huang et al. | |
| 5,149,720 A | 9/1992 | DesMarais et al. | |
| 5,158,819 A | 10/1992 | Goodman, Jr. et al. | |
| 5,165,152 A | 11/1992 | Kramer et al. | |
| 5,192,606 A | 3/1993 | Proxmire et al. | |
| 5,194,261 A | 3/1993 | Pichierri | |
| 5,197,960 A | 3/1993 | Nomura et al. | |
| 5,198,472 A | 3/1993 | DesMarais et al. | |
| 5,207,662 A | 5/1993 | James | |
| 5,217,447 A | 6/1993 | Gagnon | |
| 5,224,405 A | 7/1993 | Pohjola | |
| 5,236,428 A | 8/1993 | Zajaczkowski | |
| 5,246,431 A | 9/1993 | Minetola et al. | |
| 5,250,576 A | 10/1993 | DesMarais et al. | |
| 5,260,345 A | 11/1993 | DesMarais et al. | |
| 5,262,223 A | 11/1993 | Palumbo et al. | |
| 5,268,224 A | 12/1993 | DesMarais et al. | |
| 5,284,703 A | 2/1994 | Everhart et al. | |
| 5,292,777 A | 3/1994 | DesMarais et al. | |
| 5,306,267 A | 4/1994 | Hahn et al. | |
| 5,318,554 A | 6/1994 | Young et al. | |
| 5,324,277 A | 6/1994 | Daugan et al. | |
| 5,331,015 A | 7/1994 | DesMarais et al. | |
| 5,334,152 A | 8/1994 | Nomura et al. | |
| 5,350,624 A | 9/1994 | Georger et al. | |
| 5,352,711 A | 10/1994 | DesMarais | |
| 5,364,382 A | 11/1994 | Latimer et al. | |
| 5,387,207 A | 2/1995 | Dyer et al. | |
| 5,429,629 A | 7/1995 | Latimer et al. | |
| 5,435,806 A | 7/1995 | Daugan et al. | |
| 5,451,442 A | 9/1995 | Pieniak et al. | |
| 5,462,537 A * | 10/1995 | Carr et al. | 604/368 |
| 5,466,409 A | 11/1995 | Partridge et al. | |
| 5,466,724 A | 11/1995 | Volke et al. | |
| 5,479,945 A | 1/1996 | Simon | |
| 5,483,976 A | 1/1996 | McLaughlin et al. | |
| 5,486,166 A | 1/1996 | Bishop et al. | |
| 5,490,846 A | 2/1996 | Ellis et al. | |
| 5,506,035 A | 4/1996 | Van Phan et al. | |
| 5,509,427 A | 4/1996 | Simon et al. | |
| 5,509,915 A | 4/1996 | Hanson et al. | |
| 5,513,660 A | 5/1996 | Simon et al. | |
| 5,520,673 A | 5/1996 | Yarbrough et al. | |
| 5,527,300 A | 6/1996 | Sauer | |
| 5,527,302 A * | 6/1996 | Endres et al. | 604/385.21 |
| 5,534,561 A | 7/1996 | Volke | |
| 5,536,350 A | 7/1996 | Klemp | |
| 5,540,672 A | 7/1996 | Roessler et al. | |
| 5,556,392 A | 9/1996 | Koczab | |
| 5,562,650 A | 10/1996 | Everett et al. | |
| 5,569,229 A | 10/1996 | Rogers | |
| 5,593,401 A | 1/1997 | Sosalla et al. | |
| 5,597,437 A | 1/1997 | Lange et al. | |
| 5,601,547 A | 2/1997 | Kato et al. | |
| 5,611,879 A | 3/1997 | Morman | |
| 5,618,529 A | 4/1997 | Pichierri | |
| 5,622,584 A | 4/1997 | Kroyer | |
| 5,634,915 A | 6/1997 | Österdahl | |
| 5,645,542 A | 7/1997 | Anjur et al. | |
| 5,645,543 A | 7/1997 | Nomura et al. | |
| 5,649,919 A | 7/1997 | Roessler et al. | |
| 5,649,920 A | 7/1997 | Lavon et al. | |
| 5,652,194 A | 7/1997 | Dyer et al. | |
| 5,660,666 A | 8/1997 | Dilnik et al. | |
| 5,665,396 A | 9/1997 | Ulman | |
| 5,672,164 A | 9/1997 | Crane | |
| 5,672,166 A | 9/1997 | Vandemoortele | |
| 5,681,873 A | 10/1997 | Norton et al. | |
| 5,683,376 A | 11/1997 | Kato et al. | |
| 5,690,626 A | 11/1997 | Suzuki et al. | |
| 5,693,038 A | 12/1997 | Suzuki et al. | |
| 5,695,488 A | 12/1997 | Sosalla | |
| 5,695,846 A | 12/1997 | Lange et al. | |
| 5,711,832 A | 1/1998 | Glaug et al. | |
| 5,714,027 A | 2/1998 | Taub | |
| 5,716,703 A | 2/1998 | Payne | |
| 5,724,994 A | 3/1998 | Simon et al. | |
| 5,728,085 A | 3/1998 | Widlund et al. | |
| 5,730,737 A | 3/1998 | Widlund et al. | |
| 5,749,863 A | 5/1998 | Payne | |
| 5,752,525 A | 5/1998 | Simon et al. | |
| 5,762,641 A | 6/1998 | Bewick-Sonntag et al. | |
| 5,766,389 A | 6/1998 | Brandon et al. | |
| 5,769,091 A | 6/1998 | Simon et al. | |
| 5,810,799 A | 9/1998 | Slater | |
| 5,814,034 A | 9/1998 | Widlund et al. | |
| 5,817,085 A | 10/1998 | Widlund et al. | |
| 5,818,719 A | 10/1998 | Brandon et al. | |
| 5,827,260 A | 10/1998 | Suzuki et al. | |
| 5,830,202 A | 11/1998 | Bogdanski et al. | |
| 5,830,555 A | 11/1998 | Srinivasan et al. | |
| 5,836,929 A | 11/1998 | Bewick-Sonntag et al. | |
| 5,843,064 A | 12/1998 | Koczab | |
| 5,849,002 A | 12/1998 | Carlos et al. | |
| 5,853,402 A | 12/1998 | Faulks et al. | |
| 5,865,825 A | 2/1999 | Schlinz | |
| 5,876,394 A | 3/1999 | Rosch et al. | |
| 5,879,344 A | 3/1999 | Koczab | |
| 5,930,139 A | 7/1999 | Chapdelaine et al. | |
| 5,938,648 A | 8/1999 | LaVon et al. | |
| 5,948,434 A | 9/1999 | Labrie | |
| 5,961,757 A | 10/1999 | Trombetta et al. | |
| 5,964,970 A | 10/1999 | Woolwine et al. | |
| 5,980,087 A | 11/1999 | Brandon et al. | |
| 5,994,614 A | 11/1999 | Wada et al. | |
| 6,006,504 A | 12/1999 | Myers et al. | |
| 6,033,502 A | 3/2000 | Coenen et al. | |
| 6,049,024 A | 4/2000 | Thomas et al. | |
| 6,050,984 A * | 4/2000 | Fujioka et al. | 604/385.201 |
| 6,059,762 A | 5/2000 | Boyer et al. | |
| 6,066,775 A | 5/2000 | Bachar | |
| 6,075,178 A | 6/2000 | La Wilhelm et al. | |
| 6,092,002 A | 7/2000 | Kastman et al. | |
| 6,107,539 A | 8/2000 | Palumbo et al. | |
| 6,152,904 A | 11/2000 | Matthews et al. | |
| 6,174,302 B1 | 1/2001 | Kumasaka | |
| 6,183,587 B1 | 2/2001 | McFall et al. | |
| 6,231,557 B1 | 5/2001 | Krautkramer et al. | |
| 6,245,168 B1 | 6/2001 | Coenen et al. | |
| 6,278,037 B1 | 8/2001 | Schmidt et al. | |
| 6,298,610 B2 | 10/2001 | Traxler | |

| | | | |
|---|---|---|---|
| 6,330,735 B1 | 12/2001 | Hahn et al. | |
| 6,336,921 B1 | 1/2002 | Kato et al. | |
| 6,350,256 B1 | 2/2002 | Palumbo et al. | |
| 6,350,332 B1 | 2/2002 | Thomas et al. | |
| 6,352,528 B1 | 3/2002 | Weber et al. | |
| 6,359,192 B1 | 3/2002 | Schmidt et al. | |
| 6,362,389 B1 | 3/2002 | McDowall et al. | |
| 6,371,976 B1 | 4/2002 | Vrzalik et al. | |
| 6,395,029 B1 | 5/2002 | Levy | |
| 6,398,768 B1 | 6/2002 | Palumbo et al. | |
| 6,406,464 B1 | 6/2002 | Palumbo et al. | |
| 6,416,697 B1 | 7/2002 | Venturino et al. | |
| 6,437,212 B1 | 8/2002 | La Fortune | |
| 6,446,495 B1 | 9/2002 | Herrlein et al. | |
| 6,447,497 B1 | 9/2002 | Olson | |
| 6,453,628 B2 | 9/2002 | Traxler | |
| 6,482,412 B1 | 11/2002 | Tanaka et al. | |
| 6,506,186 B1 | 1/2003 | Roessler et al. | |
| 6,506,187 B1 | 1/2003 | Andersson et al. | |
| 6,508,797 B1 | 1/2003 | Pozniak et al. | |
| 6,514,187 B2 | 2/2003 | Coenen et al. | |
| 6,531,015 B1 | 3/2003 | Gardner, Jr. | |
| 6,551,431 B2 | 4/2003 | Lee | |
| 6,554,816 B1 | 4/2003 | Olson | |
| 6,562,167 B2 | 5/2003 | Coenen et al. | |
| 6,565,691 B2 | 5/2003 | Tomsovic et al. | |
| 6,570,057 B1 | 5/2003 | Schmidt et al. | |
| 6,573,423 B1 | 6/2003 | Herrlein et al. | |
| 6,575,953 B2 | 6/2003 | Olson | |
| 6,579,275 B1 | 6/2003 | Pozniak et al. | |
| 6,582,413 B2 | 6/2003 | Krautkramer et al. | |
| 6,596,920 B2 | 7/2003 | Wehner et al. | |
| 6,602,233 B1 | 8/2003 | Palumbo et al. | |
| 6,632,209 B1 | 10/2003 | Chmielewski | |
| 6,645,190 B1 | 11/2003 | Olson et al. | |
| 6,646,180 B1 | 11/2003 | Chmielewski | |
| 6,664,439 B1 | 12/2003 | Arndt et al. | |
| 6,676,648 B2 | 1/2004 | Bruemmer Prestley et al. | |
| 6,686,512 B1 | 2/2004 | Herrlein et al. | |
| 6,713,661 B1 | 3/2004 | Arndt et al. | |
| 6,720,471 B1 | 4/2004 | Arndt et al. | |
| 2001/0000370 A1 | 4/2001 | Traxler | |
| 2001/0000371 A1 | 4/2001 | Traxler | |
| 2001/0025164 A1 | 9/2001 | Krautkramer et al. | |
| 2001/0031957 A1 | 10/2001 | Prestley et al. | |
| 2001/0055682 A1* | 12/2001 | Ortega et al. | 428/371 |
| 2002/0095131 A1 | 7/2002 | Olson | |
| 2002/0143304 A1 | 10/2002 | Elder et al. | |
| 2003/0042660 A1 | 3/2003 | Venturino et al. | |
| 2003/0060794 A1 | 3/2003 | Olson | |
| 2003/0114814 A1 | 6/2003 | Baker et al. | |
| 2003/0153885 A1 | 8/2003 | Herrlein et al. | |
| 2003/0187413 A1 | 10/2003 | Fell | |
| 2003/0199843 A1 | 10/2003 | Kato et al. | |
| 2004/0064126 A1 | 4/2004 | Fletcher et al. | |

FOREIGN PATENT DOCUMENTS

| | | | |
|---|---|---|---|
| EP | 0432882 A3 | 6/1991 | |
| EP | 0558070 B1 | 9/1993 | |
| EP | 0610638 A1 | 8/1994 | |
| EP | 0611607 A1 | 8/1994 | |
| EP | 0631767 A1 | 1/1995 | |
| EP | 0635545 A2 | 1/1995 | |
| EP | 0635545 A3 | 1/1995 | |
| EP | 0822794 B1 | 2/1998 | |
| EP | 0951881 A2 | 10/1999 | |
| EP | 0951881 A3 | 10/1999 | |
| FR | 2604064 A1 | 3/1988 | |
| GB | 830361 | 3/1960 | |
| GB | 1375331 | 11/1974 | |
| GB | 2174037 A | 10/1986 | |
| GB | 2195541 | 4/1988 | |
| GB | 2195541 A | * | 4/1988 |
| WO | WO 9304653 A1 | 3/1993 | |
| WO | WO 9305742 A1 | 4/1993 | |
| WO | WO 9415563 A1 | 7/1994 | |
| WO | WO 9532699 A1 | 12/1995 | |
| WO | WO 9603953 A1 | 2/1996 | |
| WO | WO 9633679 A1 | 10/1996 | |
| WO | WO 9723186 A1 | 7/1997 | |
| WO | WO 9725947 A1 | 7/1997 | |
| WO | WO 9916401 A1 | 4/1999 | |
| WO | WO 9925284 A1 | 5/1999 | |
| WO | WO 9925300 A1 | 5/1999 | |
| WO | WO 9933421 A1 | 7/1999 | |
| WO | WO 9945876 A1 | 9/1999 | |
| WO | WO 9947092 A1 | 9/1999 | |
| WO | WO 0002511 A1 | 1/2000 | |
| WO | WO 0035395 A2 | 6/2000 | |
| WO | WO 0035395 A3 | 6/2000 | |
| WO | WO 0037016 A1 | 6/2000 | |
| WO | WO 02091972 A1 | 11/2002 | |
| WO | WO 02092898 A1 | 11/2002 | |

OTHER PUBLICATIONS

Search Report and Written Opinion for PCT/US2004/019448, Sep. 21, 2004.

PCT Search Report and Written Opinion for PCT/US2004/013999, Sep. 21, 2004.

PCT Search Report and Written Opinion for PCT/US2004/013998, Sep. 14, 2004.

Neubauer, et al., U.S. Appl. No. 10/721,834, filed Nov. 24, 2003, Zoned Absorbent Structures and Process for Producing Same.

Neubauer, et al., U.S. Appl. No. 10/723,304, filed Nov. 24, 2003, Quick Change Gender Specific Forming Surface and Method of Using Same.

* cited by examiner

FOLDED ABSORBENT PRODUCT

BACKGROUND OF THE INVENTION

Many types of disposable consumer products such as diapers, training pants, feminine care articles, incontinence articles, and the like, utilize an absorbent pad structure for absorbing and wicking away bodily fluids. The absorbent pads are conventionally formed from an absorbent web, typically a non-woven fibrous web material. With one particular general practice, the absorbent web is formed by employing conventional airlaying techniques wherein fibers and typically a superabsorbent material are mixed and entrained in an air stream and then directed onto a forming surface to form the web. The absorbent web may then be directed for further processing and assembly with other components to produce a final absorbent article. An advantage of this practice is that trim waste can be immediately recycled by returning the waste to the upstream fiberizing equipment and/or airlaying equipment.

With another conventional technique, preformed absorbent web sheets or layers are delivered into a manufacturing line from a preformed supply, such as a supply roll. The absorbent sheet material may be separated into adjacent strips having various configurations of repeat pattern "nested" shaped pads wherein the shape of one pad is substantially nested with the shape of at least one immediately adjacent pad.

The preformed absorbent material roll process presents particular challenges. For example, the geographical separation of the base roll-making machine makes recycling of the trim waste impractical and cost prohibitive. In this regard, the nesting feature mentioned above has been desirable to reduce the amount of waste that is generated from the originally supplied (roll) of absorbent web. However, with conventional nesting techniques and profiles, a considerable amount of trim waste is still generated.

In some applications, it may be desirable to provide a higher basis weight of absorbent material in the crotch portion as compared to the front and back portions. This has been conventionally done by using a forming surface in an air forming process that contains pockets. The pockets have a depth greater than other portions of the forming surface. Thus, during the air forming process, fibers and absorbent particles collect in the pockets creating greater basis weight areas.

Unfortunately, the pockets cannot be filled completely without overfilling the non-pocket regions. Consequently, the formed fibrous web has to be scarfed in order to remove absorbent material in the non-pocket regions. The scarfed fibrous material is then returned to the forming chamber and reused.

In addition to having to scarf the final product, use of a pocketed forming surface has also other limitations. For instance, basis weight ratios are limited by the process. Further, scarfing cannot practically be performed when various components are contained in the fibrous material that is used to form the absorbent layer. For instance, scarfing is not well suited for absorbent structures with very high superabsorbent material/fluff ratios or absorbents with components such as meltblown fibers, which may be added in certain situations to improve integrity.

The present invention provides a method for producing longitudinally symmetric or asymmetric absorbent pad structures with minimal or zero waste. The pad structures may be formed in an inline process that produces absorbent garments or, alternatively, an absorbent material may first be formed and later converted into the absorbent pad structures of the present invention for use in absorbent garments. The absorbent structures made according to the present invention have high basis weight areas at desired locations.

SUMMARY OF THE INVENTION

Various features and advantages of the invention will be set forth in part in the following description, or may be obvious from the description, or may be learned through practice of the invention.

The present invention provides an improved method for making absorbent structures for use in various applications of consumer disposable absorbent articles, such as disposable diapers, child's training pants, feminine care articles including but not limited to interlabial products, incontinence articles, swim pants, and the like.

For example, in one embodiment, the present invention is directed to an absorbent article including an outer cover material, a liner, and an absorbent structure positioned between the outer cover material and the liner. According to the present invention, the absorbent structure includes a front portion, a rear portion, and a middle portion. The absorbent structure further includes a pair of opposing lateral flaps that have been folded onto at least the middle portion of the absorbent structure. Each of the flaps, when in an unfolded state, extend beyond the width of the front portion. Further, each of the flaps have a width adjacent to the middle portion that is from about 25% to 100% of the width of the middle portion. For instance, in one embodiment, the flaps have a width adjacent to the middle portion that is from about 33% to 100% of the width of the middle portion, while in another embodiment, the flaps have a width that is from about 50% to 100% of the width of the middle portion.

Of particular advantage, by having a width that extends beyond the width of the front portion, each of the lateral flaps may be easily folded onto the absorbent structure by, for instance, a stationary folding device. Another advantage to the present invention is that the lateral flaps, when folded, produce higher basis weight areas on the absorbent structure. For example, in most applications, the lateral flaps are folded onto the middle portion creating a middle portion having a basis weight that may be higher than the basis weight of the front portion or the rear portion. The basis weight differential can vary widely depending upon the manner in which the absorbent material is formed and the size and shape of the lateral flaps. For instance, the middle portion may have a basis weight that is from about 25% greater to over 300% greater than the basis weight of the front portion and/or the rear portion. Depending upon the size of the flaps, once the flaps are folded, the middle portion may include two layers of material or may include three layers of material.

Basis weight differentials may be formed on the absorbent structure according to the present invention from a fibrous web that has a substantially uniform basis weight. Thus, greater basis weight areas may be formed on the absorbent structure without having to use a 3-dimensional forming surface and without having to scarf the absorbent fibrous web after it is formed.

In other embodiments, however, the absorbent structures of the present invention may be formed from fibrous webs that, prior to folding the lateral flaps, already have an existing basis weight differential over the surface area of the web, including absorbent webs that have been formed using a 3-dimensional forming surface. By using an absorbent web already containing a basis weight differential, the lateral flaps may be used to further increase basis weight differentials or to vary them in a desired manner.

Absorbent webs that may be used in the present invention in addition to absorbent webs having a uniform basis weight include absorbent webs having a thicker middle portion than the front or rear portion, absorbent webs having a thicker front or rear portion in relation to a middle portion, absorbent webs formed from a pocketed forming fabric thus having a relatively thick area that may vary in thickness and basis weight in the cross machine direction, and absorbent webs that contain depressions or wells that are used to form basis weight differentials. As used herein, the machine direction refers to the direction moving from the front portion to the rear portion of the absorbent web, while the cross machine direction refers to the direction moving from side to side (see FIG. 3).

The absorbent structure may have an overall hourglass-like shape. In particular, once the lateral flaps have been folded, the middle portion may be narrower than the front portion and the rear portion.

The length of the lateral flaps may vary depending upon the particular application. For instance, in one embodiment, the lateral flaps may extend only a portion of the entire length of the absorbent structure. In this embodiment, the lateral flaps are connected to the middle portion and are separated from the front portion by a first slit and separated from the rear portion by a second slit. The first slits and the second slits may be substantially perpendicular to a longitudinal axis of the absorbent structure may be diagonal to the longitudinal axis or may have any suitable non-linear or curved shape.

In another embodiment, the lateral flaps may extend the entire length of the absorbent structure. In this embodiment, the lateral flaps are separated from the front portion by a first pair of opposing slits and are separated from the rear portion by a second pair of opposing slits. The first pair of opposing slits generally extend in the lengthwise direction along the front portion and then are directed inwards towards the middle portion. Similarly, the second pair of opposing slits generally extend in a lengthwise direction along the rear portion and then are directed inwards towards the middle portion.

When the lateral flaps extend the entire length of the absorbent structure, various unique basis weight differentials can be formed in the product. For instance, absorbent structures may be formed that have a middle portion comprising two or three layers. The front and rear portion, on the other hand, may include areas comprised of a single layer and areas comprised of two layers.

Thus, when formed from an absorbent web material having a uniform basis weight, once the lateral flaps are folded, the middle portion may have a basis weight that is at least twice the basis weight of areas of the front portion and the rear portion, and, in one embodiment, at least 3 times the basis weight of areas of the front portion and the rear portion. In this embodiment, the front portion and the rear portion may also include higher basis weight areas. For instance, a center area of the front portion and a center area of the rear portion may have a basis weight that is at least twice the basis weight of two opposing lateral areas on the front portion and two opposing lateral areas on the rear portion.

The basis weight differentials may be modified and varied by varying the width of the folded lateral flaps. Further, the basis weight differentials may also be modified and varied by using an absorbent web that already contains basis weight differentials as described above.

The present invention is also generally directed to a method of forming the absorbent structures described above. For instance, in one embodiment, a strip of absorbent web material is conveyed along the machine direction. The absorbent web material is cut in order to form opposing lateral flaps. The opposing lateral flaps define a widest portion of the absorbent web material.

Once formed, the opposing lateral flaps are folded onto the absorbent web material. The strip of web material is cut in a cross direction into individual absorbent pads.

The strip of absorbent web material may be formed according to any suitable process. For instance, the absorbent web material may be formed on an inline manufacturing process such as in an inline airforming process, or an off line manufacturing process such as an offline airlaid process. Processes that may be used to form the absorbent web material include an airforming process, a coform process, or a wet lay process. The absorbent web material may have a basis weight, for instance, from about 100 gsm to about 2000 gsm. In one particular embodiment, the absorbent web material contains cellulosic fibers and superabsorbent particles.

The invention will be described below in greater detail by reference to particular embodiments set forth in the figures.

DETAILED DESCRIPTION

Figure 1:
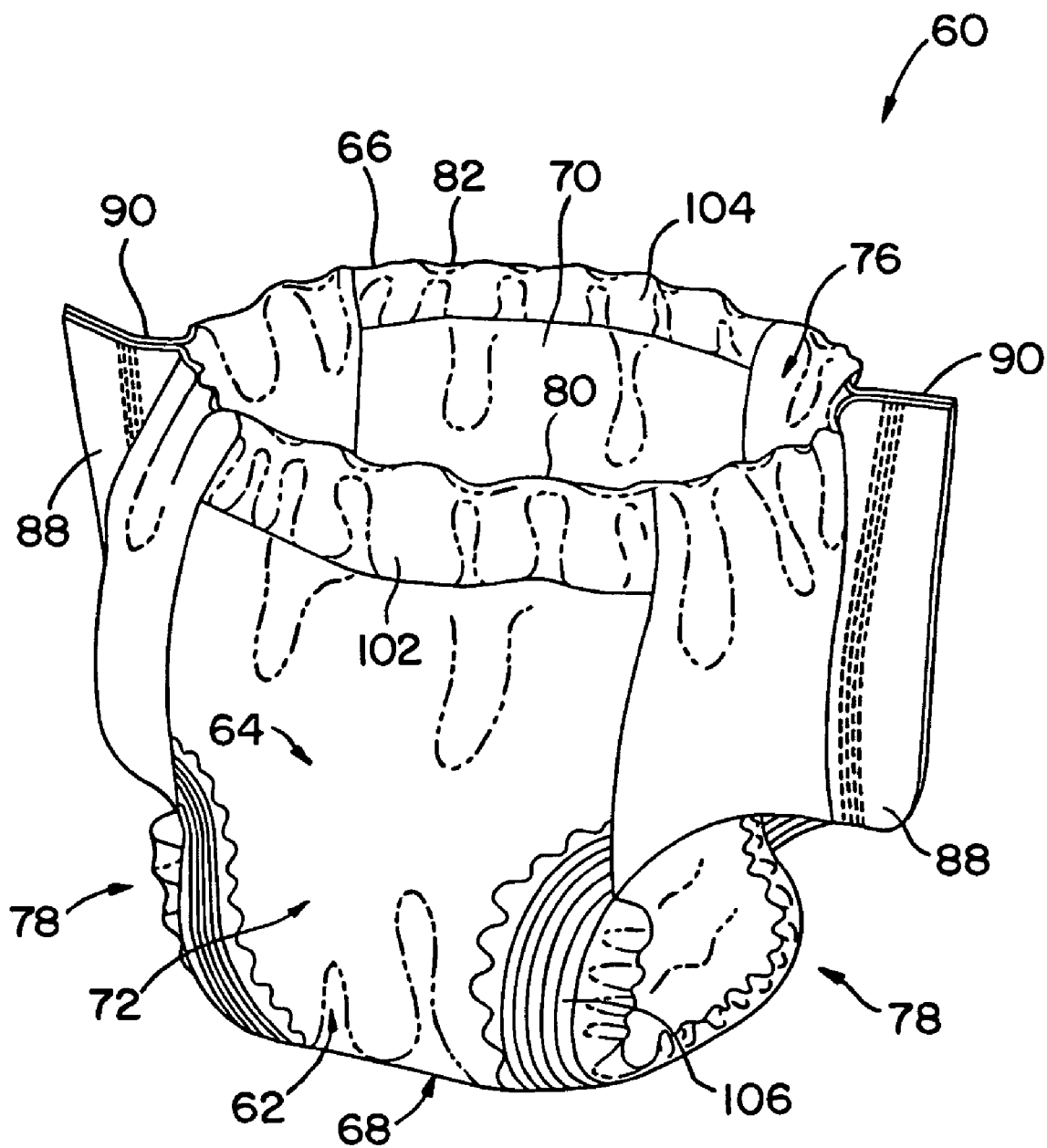
FIG. 1 is a perspective view of one embodiment of an absorbent article that may be made according to the present invention.

The invention will now be described in detail with reference to particular embodiments thereof. The embodiments are provided by way of explanation of the invention, and not meant as a limitation of the invention. For example, features described or illustrated as part of one embodiment may be used with another embodiment to yield still a further embodiment. It is intended that the present invention include these and other modifications and variations as come within the scope and spirit of the invention.

The present method is particularly suited for the manufacture of pad structures from a web of absorbent material, the pads intended for use in various consumer disposable absorbent products. Such products include, but are not limited to, diapers, child's training pants, feminine care articles (such as panty liners, pads, and interlabial products), incontinence articles, swim pants, and the like. The invention is not limited to any particular type or composition of absorbent web material, and may be practiced with any suitable absorbent web material known to those skilled in the art. The absorbent web material may include any structure and combination of components which are generally compressible, conformable, non-irritating to a wearer's skin, and capable of absorbing and retaining liquids and certain body wastes.

The absorbent structures of the present invention generally include a front portion, a middle portion and a rear portion. In accordance with the present invention, the absorbent structures further contain a pair of opposing lateral flaps that are folded onto at least the middle portion of the absorbent structure. The lateral flaps, when in an unfolded state, form the widest part of the unfolded web making it relatively easy for a stationary folding device to fold the flaps over onto the web as the web is being conveyed in the lengthwise direction. Further, the absorbent structures may be formed without producing any trim waste.

By folding the lateral flaps onto the absorbent web, greater basis weight areas can be formed into the middle portion of the absorbent structure which corresponds to the crotch region of an absorbent product incorporating the absorbent structure. Of particular advantage, the basis weight differential can be varied depending upon the width and length of the lateral flaps. Further, the basis weight differential can be formed without having to use a 3-dimensional forming surface and without having to scarf the web after the web has been formed.

The absorbent web material used to form the absorbent structures may include, for example, cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from US Alliance Pulp Mills of Coosa, Ala., USA, and is a bleached, highly absorbent wood pulp containing primarily soft wood fibers. As a general rule, the superabsorbent material is present in the absorbent web in an amount of from about 0 to about 100 weight percent based on total weight of the web. The web has a density within the range of about 0.10 to about 0.50 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a suberabsorbent material is capable of absorbing at least about 15 times its weight in liquid, and desirably is capable of absorbing more than about 25 times its weight in liquid. Suitable superabsorbent materials are readily available from various suppliers. For example, FAVOR SXM 880 superabsorbent is available from Stockhausen, Inc., of Greensboro, N.C., USA; and Drytech 2035 is available from Dow Chemical Company, of Midland Mich., USA.

Subsequent to or after being cut from the web material strip, the individual absorbent pads may be partially or wholly wrapped or encompassed by a suitable tissue or nonwoven wrap that aids in maintaining the integrity and shape of the pad. For example, in one embodiment, the absorbent web material may be formed on a tissue or nonwoven web and then later wrapped to form individual absorbent structures.

The absorbent materials may be formed into a web structure by employing various conventional methods and techniques. For example, the absorbent web may be formed with a dry-forming technique, an airlaying technique, a carding technique, a meltblown or spunbond technique, a wet-forming technique, a foam-forming technique, or the like, as well as combinations thereof. Layered and/or laminated structures may also be suitable. Methods and apparatus for carrying out such techniques are well known in the art.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles or fibers, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference for all purposes.

It is also contemplated that elastomeric absorbent web structures may be particularly useful with the present invention. For example, an elastomeric coform absorbent structure having from about 35% to about 65% by weight of a wettable staple fiber, and greater than about 35% to about 65% by weight of an elastomeric thermoplastic fiber may be used to define absorbent pad structures according to the invention. Examples of such elastomeric coform materials is provided in U.S. Pat. No. 5,645,542, incorporated herein in its entirety for all purposes. As another example, a suitable absorbent elastic nonwoven material may include a matrix of thermoplastic elastomeric nonwoven filaments present in an amount of about 3 to less than about 20% by weight of the material, with the matrix including a plurality of absorbent fibers and a superabsorbent material each constituting about 20-77% by weight of the material. U.S. Pat. No. 6,362,389 describes such a nonwoven material and is incorporated herein by reference in its entirety for all purposes. Absorbent elastic nonwoven materials are useful in a wide variety of personal care articles where softness and conformability, as well as absorbency and elasticity, are important.

The absorbent web may also be a nonwoven web comprising synthetic fibers. The web may include additional natural fibers and/or superabsorbent material. The web may have a density in the range of about 0.05 to about 0.5 grams per cubic centimeter. The absorbent web can alternatively be a foam.

In a particular aspect of the invention, the absorbent web material can be provided with an absorbent capacity of at least about 8 g/g employing 0.9 wt % saline (8 grams of 0.9 wt % saline per gram of absorbent web). The absorbent capacity of the absorbent web can alternatively be at least about 9 g/g, and can optionally be at least about 15 g/g to provide improved benefits. Additionally, the absorbent capacity may be up to about 40 g/g, or more, to provide desired performance.

In another aspect, the web of absorbent material can be provided with a tensile strength value of at least about 0.5 N/cm (Newtons per cm of "width" of the material, where the "width" direction is perpendicular to the applied force). The tensile strength of the absorbent web can alternatively be at least about 1.5 N/cm, and can optionally be at least about 2 N/cm to provide improved benefits. In another aspect, the web of absorbent material can be provided with a tensile strength value of up to a maximum of about 100 N/cm, or more. The tensile strength of the absorbent web can alternatively be up to about 10 N/cm, and can optionally be up to about 20 N/cm to provide improved benefits.

The selected tensile strength should provide adequate processibility of the web throughout the manufacturing process, and can help to produce articles that exhibit desired combinations of softness and flexibility. In particular, the absorbent web material should have a tensile strength in the cross-direction to undergo stretching as described herein without resulting in substantial degradation of the web integrity to the extent that the pad structures cannot be further processed in absorbent articles. In some cases, the stretching of the web material in the cross direction can provide a softer and more flexible material than the initial web. This is generally desired for initially stiff materials such as some stabilized airlaid or wetlaid materials.

The absorbent material web is also selected so that the individual absorbent pad structures possess a particular individual total absorbency depending on the intended article of use. For example, for infant care products, the total absorbency can be within the range of about 200-900 grams of 0.9 wt % saline, and can typically be about 500 g of 0.9 wt % saline. For adult care products, the total absorbency can be within the range of about 400-2000 grams of 0.9 wt % saline, and can typically be about 1300 g of saline. For feminine care products, the total absorbency can be within the range of about 7-50 grams of menstrual fluid or menses simulant, and can typically be within the range of about 30-40 g of menstrual fluid or menses simulant.

Figure 5:
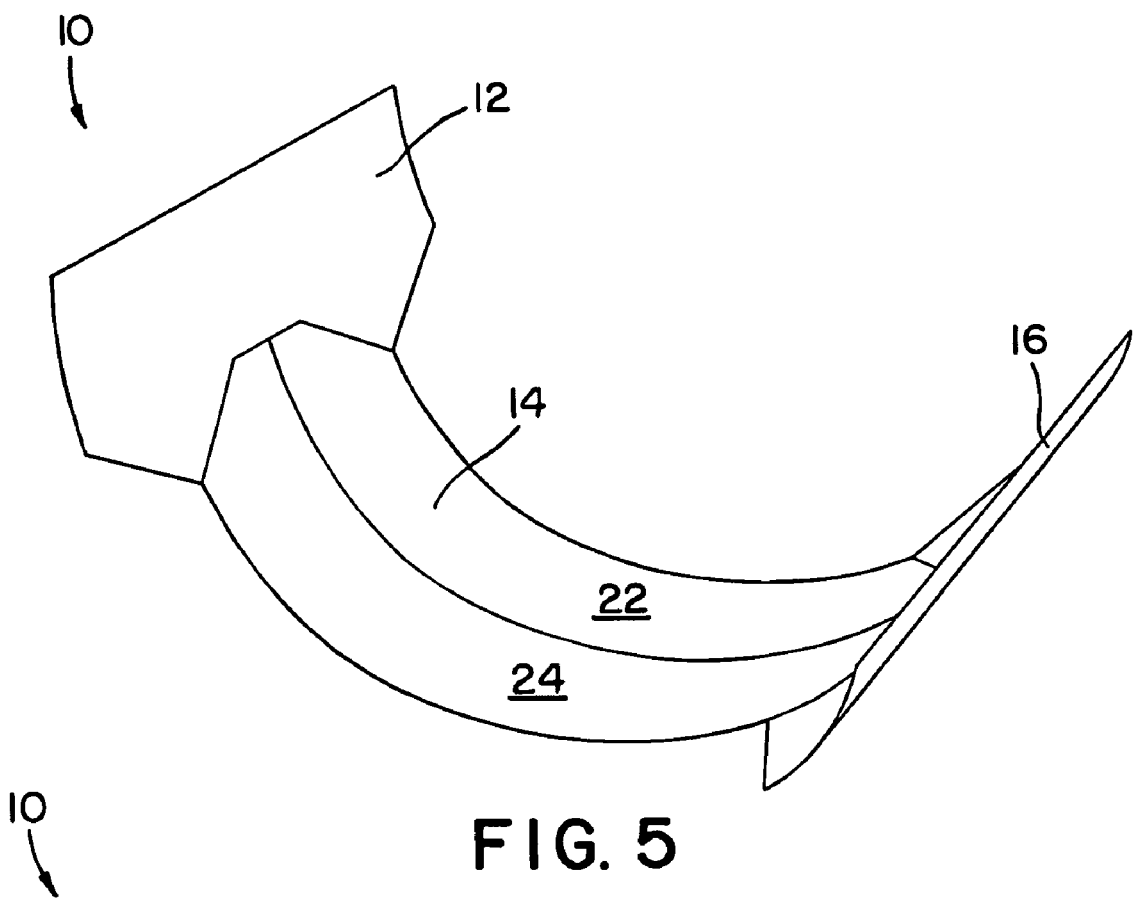
FIG. 5 is a perspective view of one embodiment of an absorbent structure made in accordance with the present invention.
Figure 6:
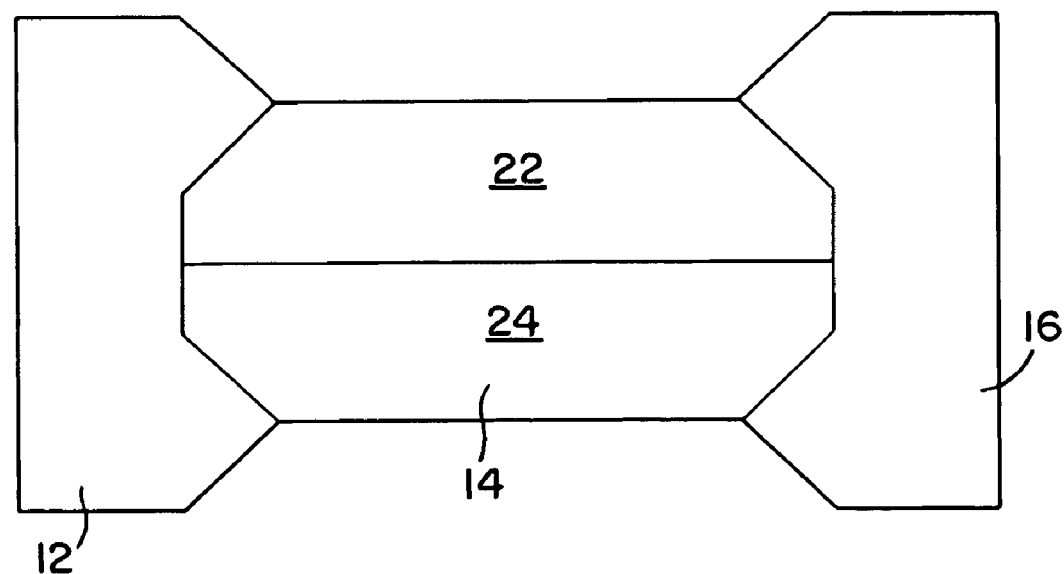
FIG. 6 is a plan view of the absorbent structure shown in FIG. 5.

Referring to FIGS. 5-6, one embodiment of an absorbent structure generally 10 made in accordance with the present invention is shown. As shown in FIGS. 5 and 6, in this embodiment, the absorbent structure 10 includes a front portion 12, a middle portion 14, and a rear portion 16. The absorbent structure 10 has a generally hourglass-like shape in that the middle portion 14 is narrower than the front portion 12 and the rear portion 16. If desired, however, the rear portion 16 may also be narrower than the front portion 12.

Figure 7:
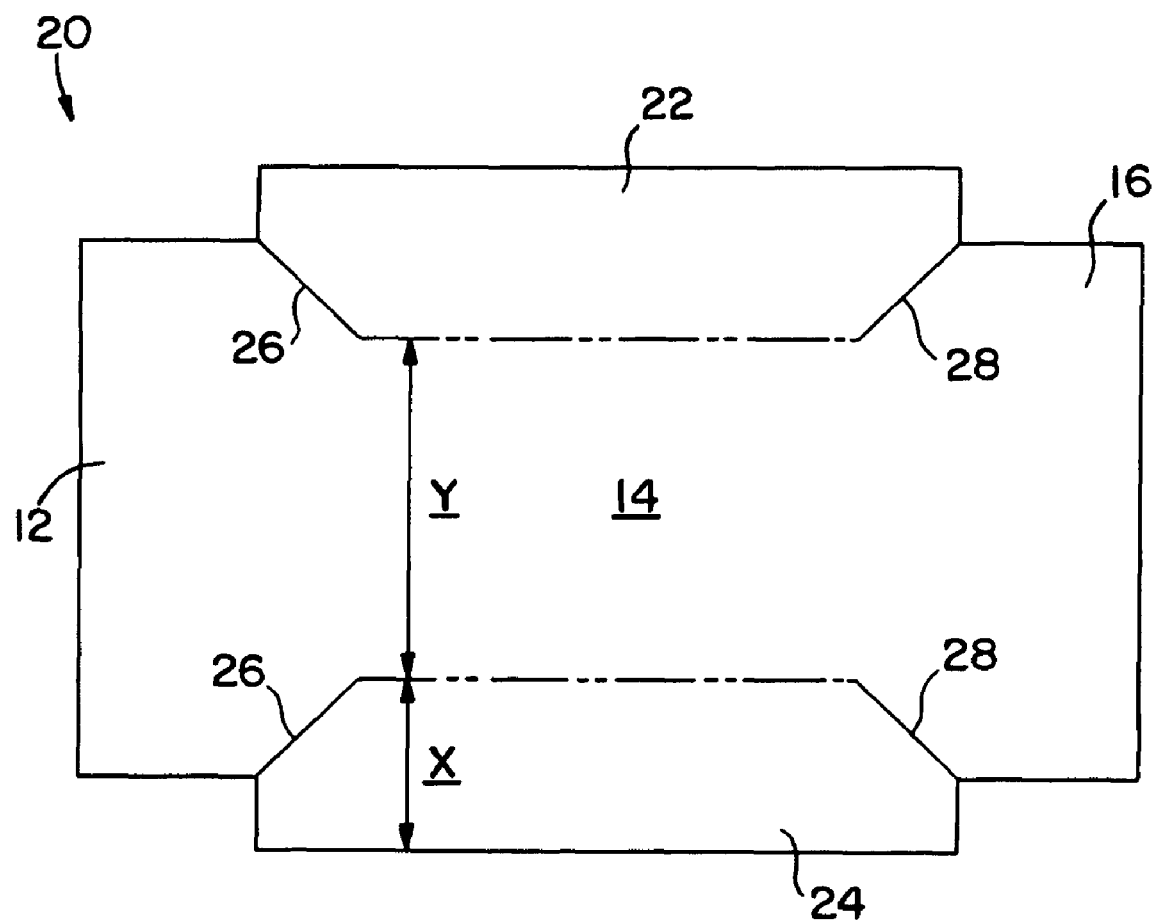
FIG. 7 is an unfolded plan view of the absorbent structure shown in FIG. 5.

Referring to FIG. 7, a blank generally 20 that may be used to form the absorbent structure 10 as shown in FIGS. 5 and 6 is illustrated. As shown, the blank 20 includes a pair of opposing lateral flaps 22 and 24. The lateral flaps 22 and 24 are each connected to the middle portion 14 of the absorbent web. The lateral flaps 22 and 24 are separated from the front portion 12 by a pair of front slits 26 and are separated from the rear portion 16 by a pair of rear slits 28. In this embodiment, the slits 26 and 28 all are diagonal to the longitudinal axis of the blank 20. Specifically, the slits 26 angle inwardly from the front portion 12 to the middle portion 14 while the slits 28 angle inwardly from the rear portion 16 to the middle portion 14. In other embodiments, however, the slits 26 and 28 may be perpendicular to the longitudinal axis of the blank 20 or may have any suitable non-linear or curved shape.

In order to form the absorbent structure 10 as shown in FIG. 5, the lateral flaps 22 and 24 are folded onto the middle portion 14. In this manner, a greater basis weight area is created in the middle portion in comparison to the basis weight of the front portion 12 and the rear portion 16, assuming that the fibrous web used to form the absorbent structure has a substantially uniform basis weight.

Referring to FIG. 7, the lateral flaps each have a width X, while the middle portion has a width Y. In this embodiment, the width of the lateral flaps is approximately one half of the width of the middle portion 14. Thus, once the lateral flaps 22 and 24 are folded, the middle portion 14 comprises two layers of material has a basis weight that is about twice the basis weight of the front portion 12 and the rear portion 16, if the blank 20 is made from an absorbent material having a generally uniform basis weight. In other embodiments, the blank 20 can be made from an absorbent material having preformed differential basis weights. For instance, the blank 20 may be made from an absorbent material that has a higher basis weight in the middle portion than in the front and rear portion. Alternatively, the absorbent material may have a basis weight differential that extends in the cross machine direction (direction 86 shown in FIG. 3). For instance, the lateral flaps may have a basis weight greater than the middle portion of the absorbent material. In another embodiment, the front and rear portion may have a basis weight greater than the middle portion. In still other embodiments, the absorbent material may be formed using a 3-dimensional forming surface that forms high basis weight pockets in the web. In still other embodiments, wells or depressions may be formed into the web for forming smaller basis weight areas. Thus, the basis weight differential between the middle portion 14 and the remainder of the absorbent structure 10 may vary widely depending upon the particular application. For example, once the lateral flaps are folded, the middle portion 14 may have a basis weight that is from about 25% to over 200% greater than the basis weight of the front portion or the rear portion.

When incorporated into an absorbent article, the middle portion 14 generally forms the crotch area of the article. Having a greater basis weight in the crotch area of an absorbent product is generally desired.

Of particular advantage, the basis weight differential, the location of the higher basis weight areas and even the fluid handling properties of the structure may be modified as desired by varying the width of the lateral flaps 22 and 24. For instance, the lateral flaps 22 and 24 may have a width X that may range from about 25% to 100% of the width Y of the middle portion 14. For example, if the width of the lateral flaps 22 and 24 were less than 50% of the width of the middle portion 14, a fluid channel forms directly in the center of the product that has a basis weight slightly less than the basis weight of the remainder of the middle portion. More importantly, the channel that is formed may be used to quickly collect fluids that are then absorbed into the remainder of the middle portion.

In alternative embodiments, the lateral flaps 22 and 24 may have a width that is greater than 50% of the width of the middle portion 14. When the lateral flaps 22 and 24, for instance, have a width greater than 50% of the width of the middle portion, the lateral flaps will overlap in the center of the absorbent structure 10. Where the flaps overlap, the middle portion 14 comprises a three layer structure. Thus, when the absorbent structure is formed from an absorbent material having a relatively uniform basis weight, folding the flaps creates a basis weight in the middle portion that is three times the basis weight of the front portion 12 or the rear portion 16.

As described above, however, non-uniform basis weight absorbent materials may also be used in forming the absorbent structure 10. Thus, the actual basis weight differential between the middle portion 14, the front portion 12, and the rear portion 16 may vary dramatically. In general, for instance, the middle portion may have a basis weight that is from about 25% to over 300% greater than the basis weight of the remainder of the absorbent structure.

Figure 12:
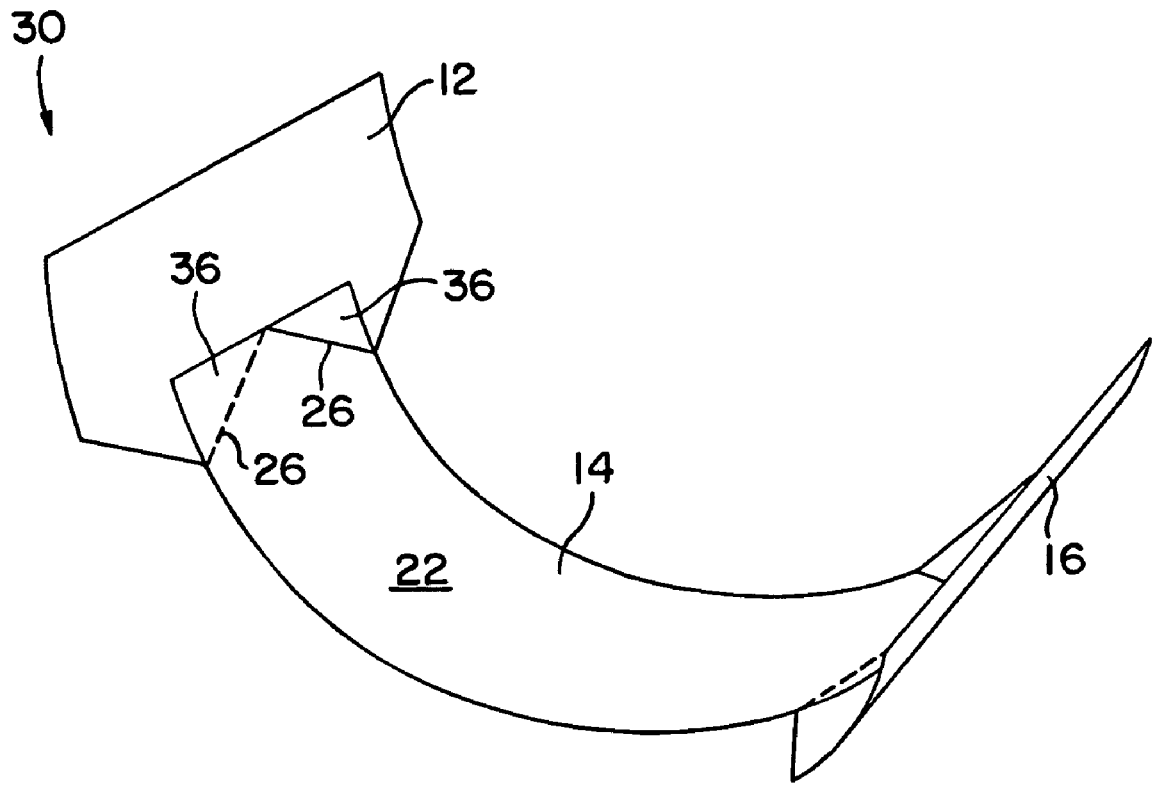
FIG. 12 is a perspective view of another embodiment of an absorbent structure made in accordance with the present invention.
Figure 13:
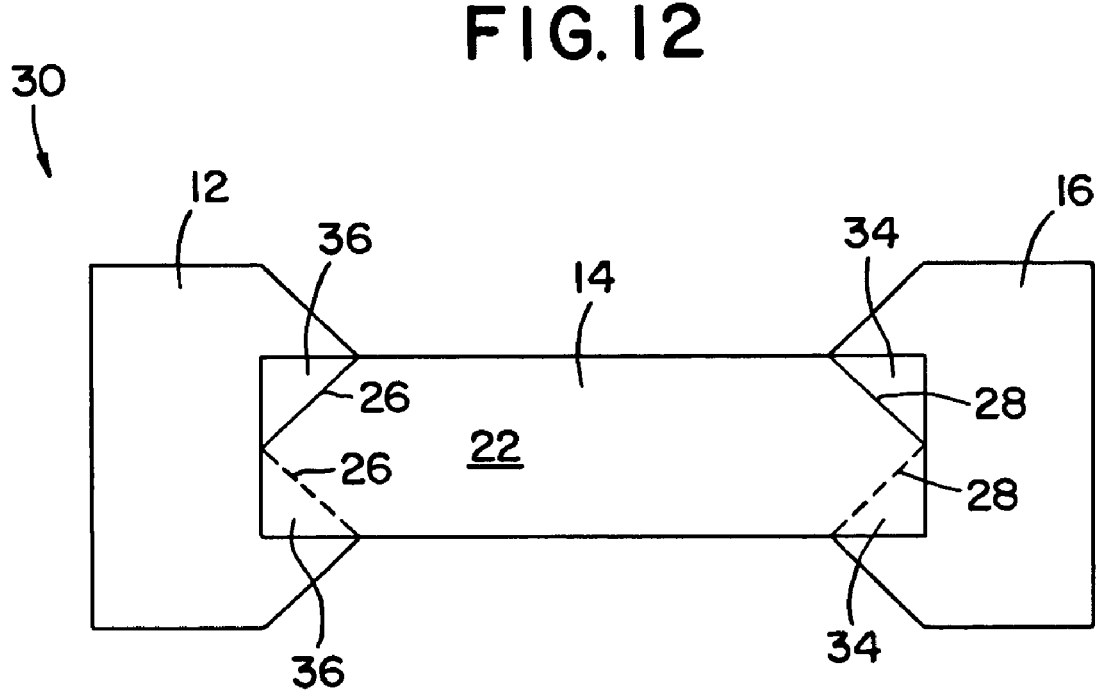
FIG. 13 is a plan view of the absorbent structure shown in FIG. 12.
Figure 14:
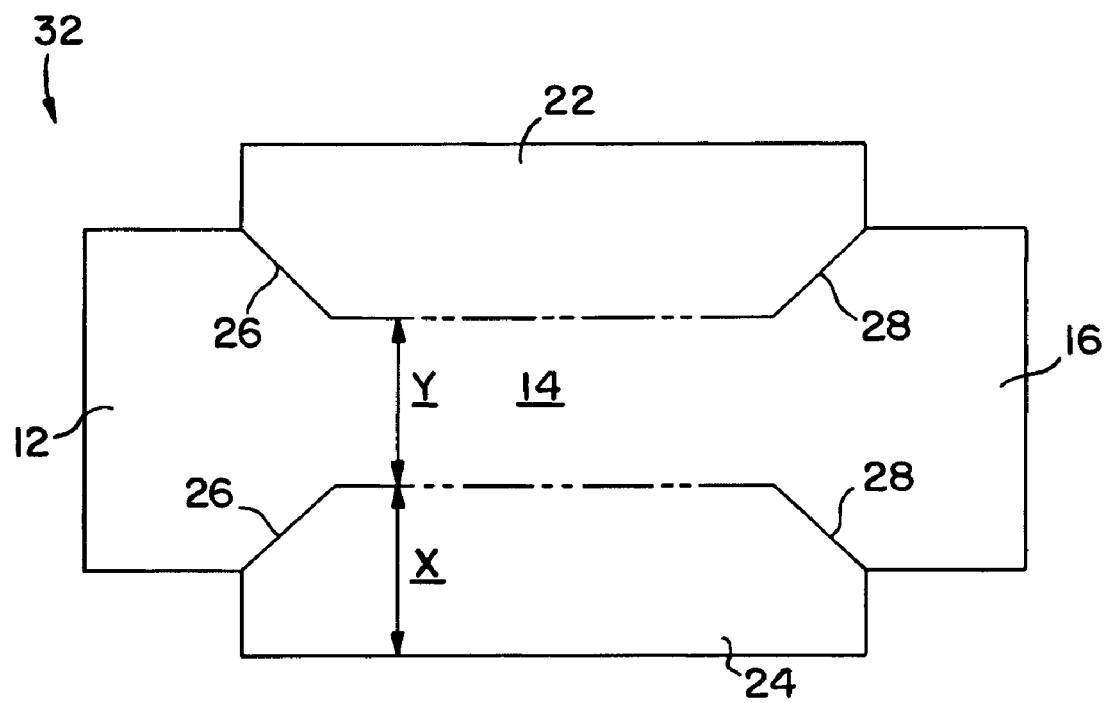
FIG. 14 is a plan view of the absorbent structure shown in FIG. 12 in an unfolded state.

For instance, referring to FIGS. 12 and 13, another embodiment of an absorbent structure generally 30 made in accordance with the present invention is shown. In FIG. 14, a blank generally 32 is illustrated that may be used to form the absorbent structure 30. In FIGS. 12-14, like reference numerals have been used to indicate similar elements.

As shown in FIG. 14, in this embodiment, the blank 32 includes a pair of opposing lateral flaps 22 and 24 that have a width X that is substantially the same width Y as a middle portion 14. In this manner, both lateral flaps 22 and 24 when folded extend across the entire width of the middle portion 14. Thus, a middle portion is formed or created that has a three layer structure and may have a basis weight that is 3 times the basis weight of the front portion 12 and the rear portion 16 if the absorbent structure is formed from an absorbent material having a relatively uniform basis weight. This 3 to 1 basis weight differential is formed according to the present invention from a web that may have a substantially uniform basis weight and without having to scarf the web.

Referring to FIGS. 12 and 13, due to the shape of the front slots 26 and the rear slots 28, triangular portions 34 and 36 are also formed. Once the lateral flaps 22 and 24 are folded, the triangular portions 34 and 36 contain two layers of material and therefore have a basis weight that is twice the basis weight of the front portion 12 and the rear portion 16.

As shown in FIGS. 7 and 14, the lateral flaps 22 and 24 of both blanks 20 and 32 form the widest portion of the fibrous web. By forming the widest portion of the web, the flaps can be easily located and folded using a stationary folding device. In fact, due to the width of the flaps, it may not be necessary to score the web prior to folding the flaps, although score lines may be formed on the absorbent web where the flaps are to be folded if desired.

Figure 18:
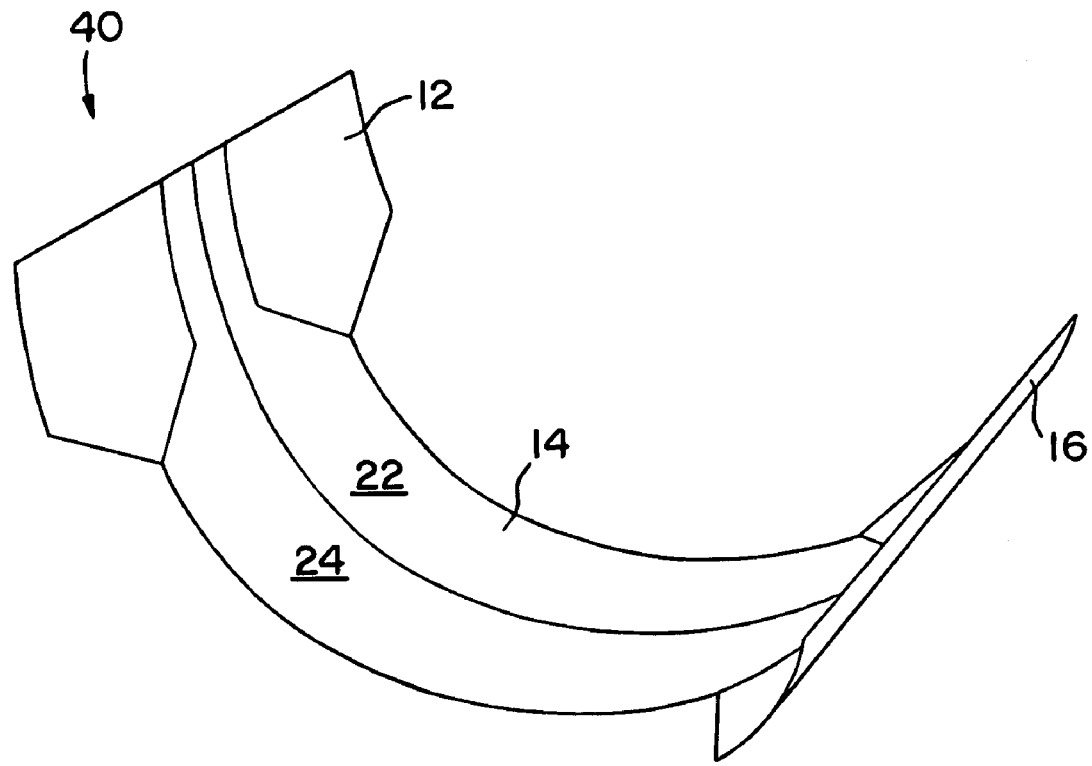
FIG. 18 is a perspective view of still another embodiment of an absorbent structure made in accordance with the present invention.
Figure 19:
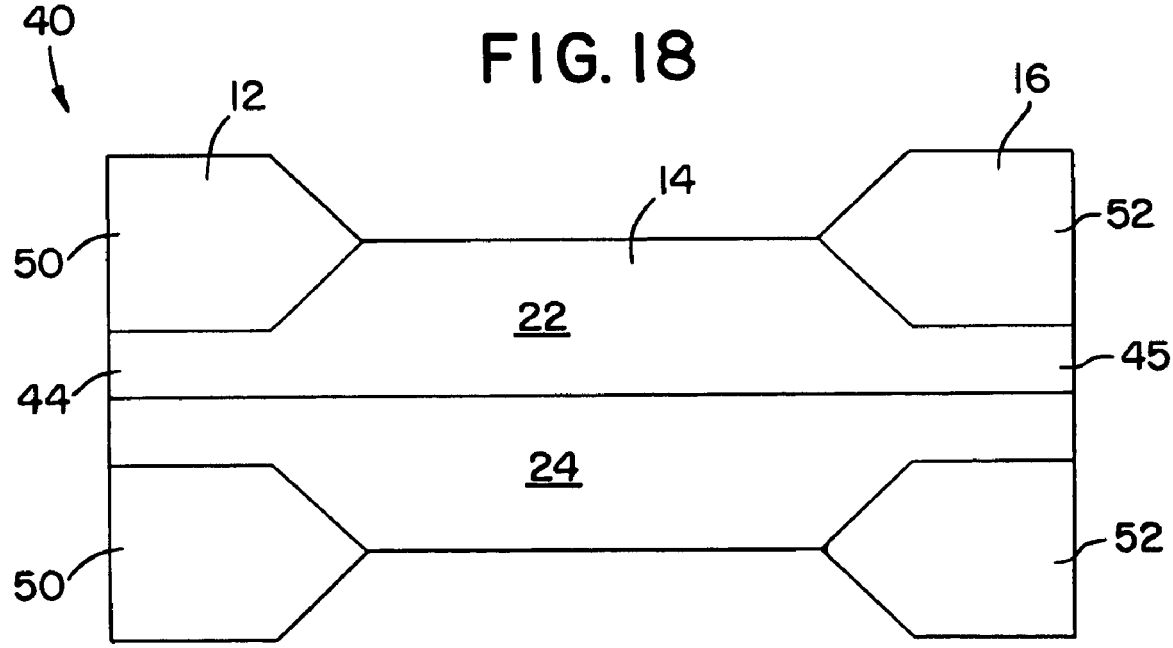
FIG. 19 is a plan view of the absorbent structure shown in FIG. 18.
Figure 20:
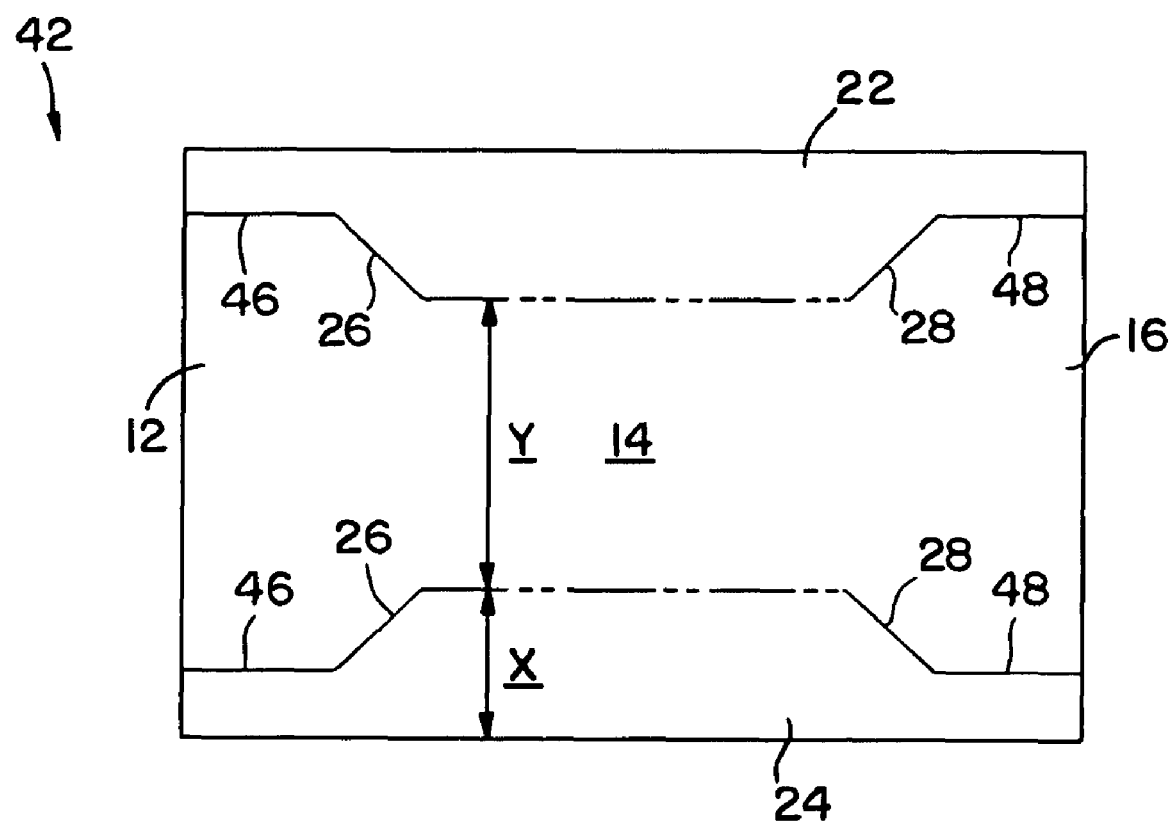
FIG. 20 is a plan view of the absorbent structure shown in FIG. 18 in an unfolded state.

Referring to FIGS. 18 and 19, still another embodiment of an absorbent structure generally 40 made in accordance with the present invention is shown. A blank generally 42 used to form the absorbent structure 40 is shown in FIG. 20. Again, like reference numerals have been used to indicate similar elements. Referring to FIG. 20, in this embodiment, the lateral flaps 22 and 24 extend the entire length of the blank 42. In order to separate the flaps 22 and 24 from the front portion 12, the blank 42 includes a pair of additional slits 46. Slits 46 extend in the lengthwise direction of the blank 42 parallel with the longitudinal axis. Similarly, in order to separate the lateral flaps 22 and 24 from the rear portion 16, the blank 42 includes a pair of opposing slits 48 that are also generally parallel to the longitudinal axis of the blank.

In this embodiment, the width X of the lateral flaps 22 and 24 is about 50% of the width Y of the middle portion 14. Referring to FIGS. 18 and 19, once the lateral flaps 22 and 24 are folded, the middle portion 14 comprises two layers of material and may have a basis weight that is about twice the basis weight of areas of the front portion 12 and areas of the rear portion 16, should the absorbent structure be formed from an absorbent web having a relatively uniform basis weight. In this embodiment, however, the front portion 12 includes a center area 44 and the rear portion 16 includes a center area 45 that are also comprised of two layers of material and thus also may have the same basis weight as the middle portion 14. Lateral areas 50 of the front portion 12 and lateral areas 52 of the rear portion 16, however, remain as a single layer of material. Thus, the middle portion 14, the center area 44 of the front portion 12 and the center area 45 of the rear portion 16 all have an increased basis weight in comparison to the lateral areas 50 of the front portion 12 and the lateral areas 52 of the rear portion 16. In this embodiment, the center areas 44 and 45 generally extend the size of the higher basis weight areas for providing greater liquid absorbency.

In the embodiments shown in FIGS. 18-20, the lateral flaps 22 and 24, similar to the embodiments shown in FIGS. 5-7, still comprise the widest portion of the blank 42. By being the widest portion of the blank 42, the lateral flaps 22 and 24 may be easily folded over onto the absorbent web as will be described in more detail below.

Figure 25:
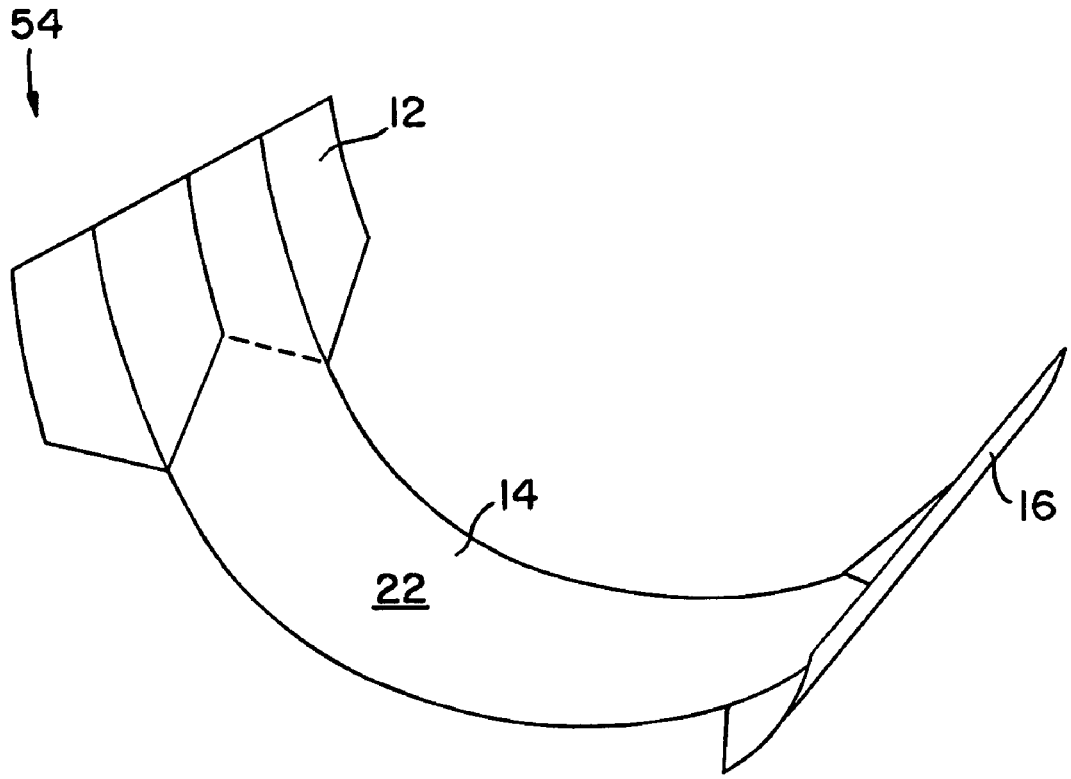
FIG. 25 is still another embodiment of an absorbent structure made in accordance with the present invention.
Figure 26:
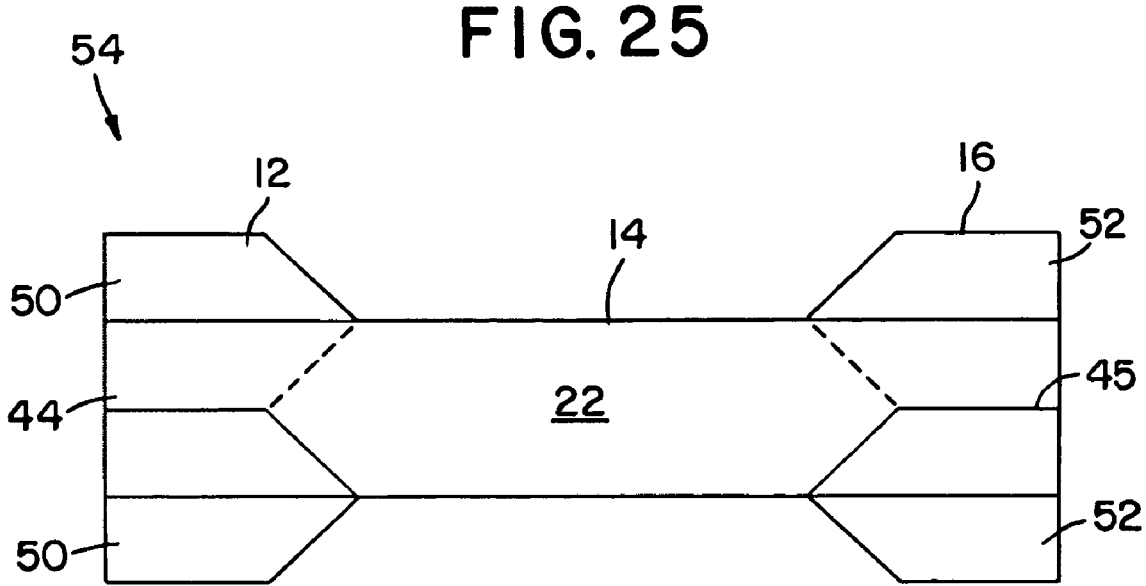
FIG. 26 is a plan view of the absorbent structure shown in FIG. 25.

Referring to FIGS. 25 and 26, another embodiment of an absorbent structure generally 54 made in accordance with the present invention is illustrated. A blank generally 56 is shown in FIG. 27 which may be used to form the absorbent structure 54 shown in FIGS. 25 and 26.

Figure 27:
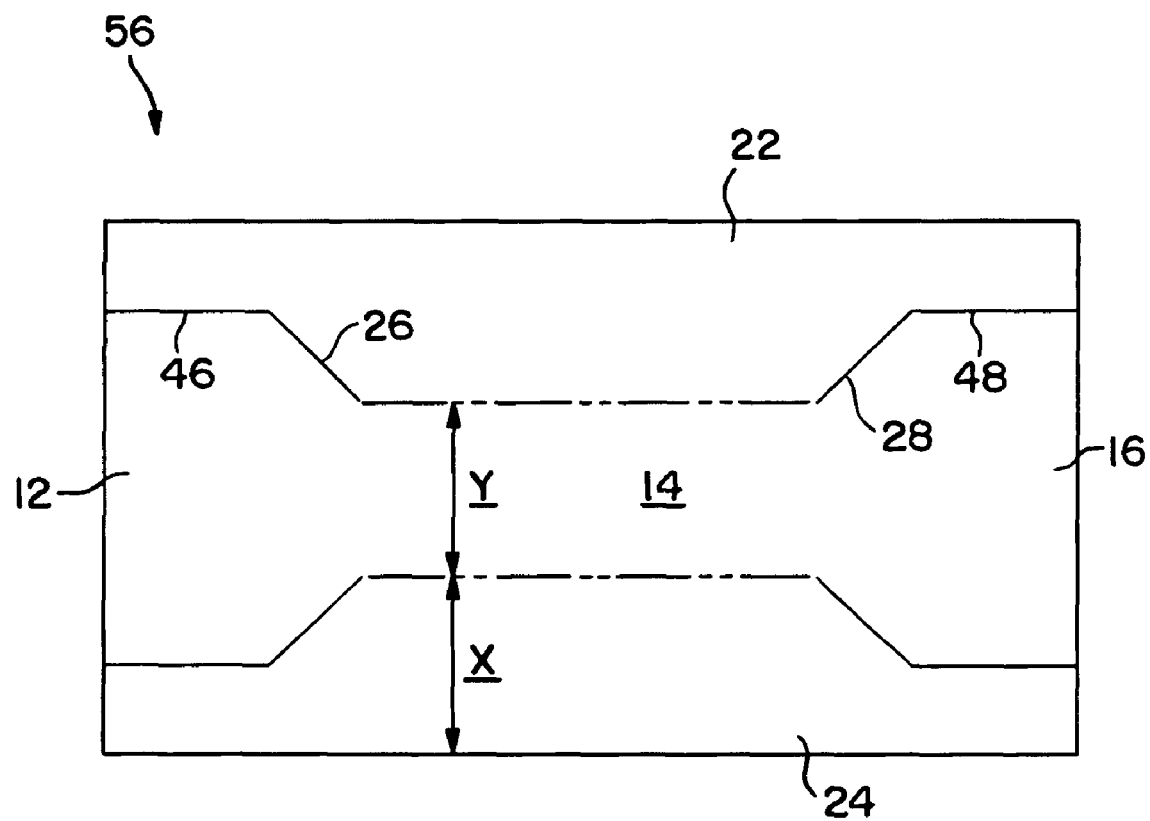
FIG. 27 is a plan view of a blank that may be used to form the absorbent structure illustrated in FIG. 25.

Referring to FIG. 27, in this embodiment, the lateral flaps 22 and 24 have a width X that is substantially equal to the width Y of the middle portion 14. Similar to the embodiment shown in FIGS. 12-14, the width of the lateral flaps 22 and 24 may be varied in order to vary the basis weight differentials that are produced when the lateral flaps are folded. For instance, the lateral flaps 22 and 24 may have a width that is generally from about 25% to 100% of the width of the middle portion. In the embodiment shown in FIG. 27, for instance, the width X of the lateral flaps is 100% of the width Y of the middle portion 14.

Once the lateral flaps 22 and 24 are folded, the absorbent structure 54 as shown in FIGS. 25 and 26 is created. As shown particularly in FIG. 26, the resulting absorbent structure 54 includes a middle portion 14, a center area 44 of the front portion 12, lateral areas 50 of the front portion 12, a center area 45 of the rear portion 16, and lateral areas 52 of the rear portion 16. By folding the lateral flaps, the middle portion 14 contains 3 layers of material, the center areas 44 and 45 contain 2 layers of material, while the lateral areas 50 and 52 contain a single layer of material. Thus, when formed from a web having a substantially uniform basis weight, the middle portion 14 has a basis weight that is 3 times the basis weight of the lateral areas 50 and 52, while the center areas 44 and 45 have a basis weight that is about twice the basis weight of the lateral areas 50 and 52. In other embodiments, however, the absorbent structure may be produced from a web having higher basis weight areas that are created during formation of the web. In these embodiments, the basis weight differentials between the middle portion, the center areas, and the lateral areas may vary depending upon the desired result.

The absorbent structures illustrated in FIGS. 5, 6, 12, 13, 18, 19, 25 and 26 are particularly well suited for incorporation into an absorbent product, such as a diaper, an adult incontinence product, or a feminine hygiene product. For example, referring to FIG. 1, a pant-like absorbent article generally 60 is illustrated. The article 60 includes a chassis 62 defining a front region 64, a back region 66, and a crotch region 68 interconnecting the front and back regions. The chassis 62 includes a bodyside liner 70 which is configured to contact the wearer, and an outer cover 72 opposite the bodyside liner which is configured to contact the wearer's clothing. An absorbent structure 74 (see FIG. 4) is positioned or located between the outer cover 72 and the bodyside liner 70. The absorbent structure 74 is made in accordance with the present invention and may be, for instance, an absorbent structure as illustrated in FIG. 5, FIG. 12, FIG. 18, or FIG. 25.

Figure 2:
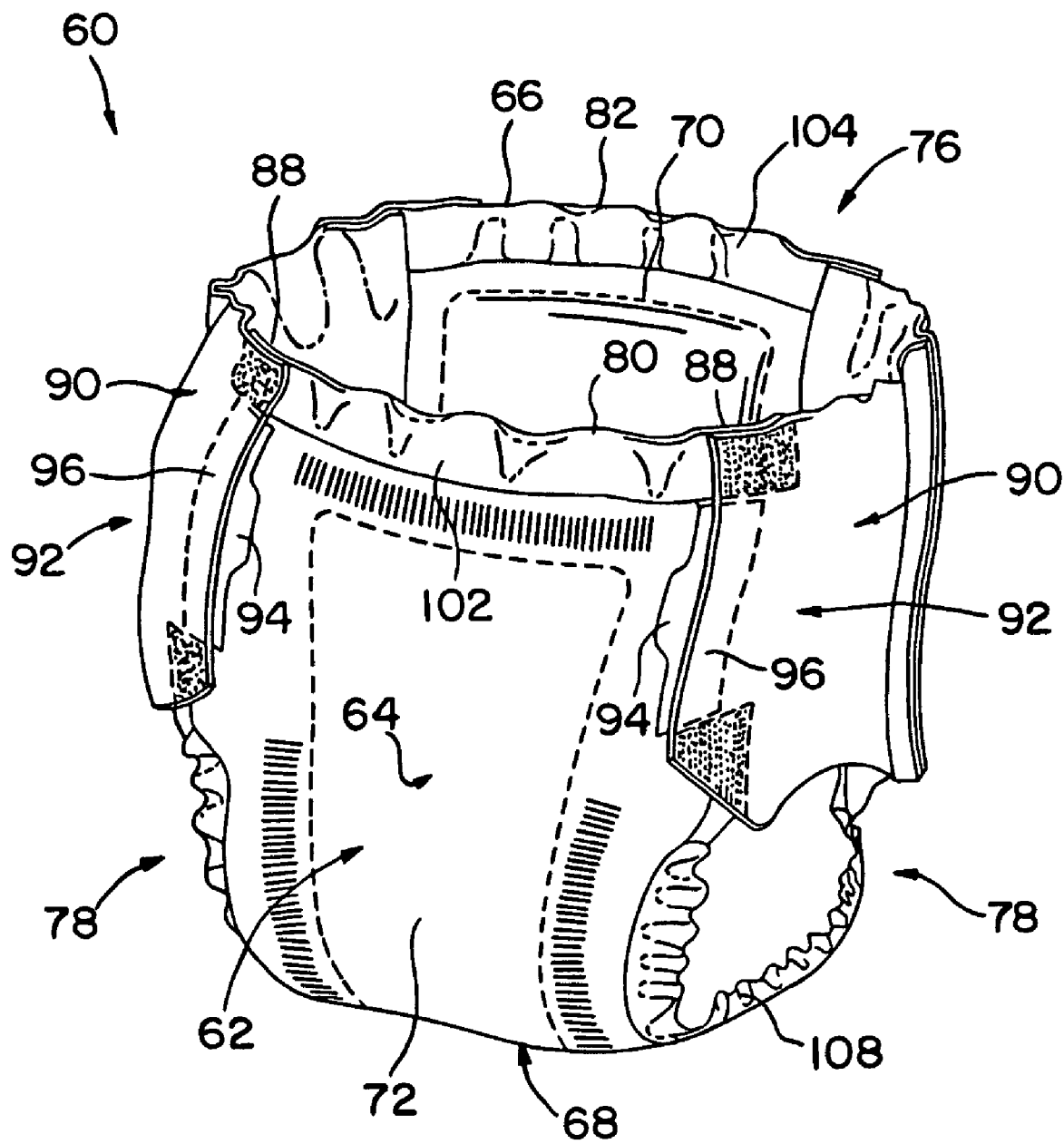
FIG. 2 is a perspective view of another embodiment of an absorbent article that may be made in accordance with the present invention.

FIG. 2 illustrates an alternative embodiment of an absorbent article 60 similar to the absorbent article illustrated in FIG. 1. Like reference numerals have been used to indicate similar elements. As shown, the absorbent article 60 shown in FIG. 2, different than the embodiment shown in FIG. 1, includes refastenable sides. The absorbent article 60 shown in FIG. 1, on the other hand, has permanently bonded sides. Both embodiments of an absorbent article define a 3-dimensional pant configuration having a waist opening 76 and a pair of leg openings 78. The front region 64 includes the portion of the article 60 which, when worn, is positioned on the front of the wearer while the back region 66 includes the portion of the article which, when worn, is positioned on the back of the wearer. The crotch region 68 of the absorbent article 60 includes the portion of the article which, when worn, is positioned between the legs of the wearer and covers the lower torso of the wearer.

Figure 3:
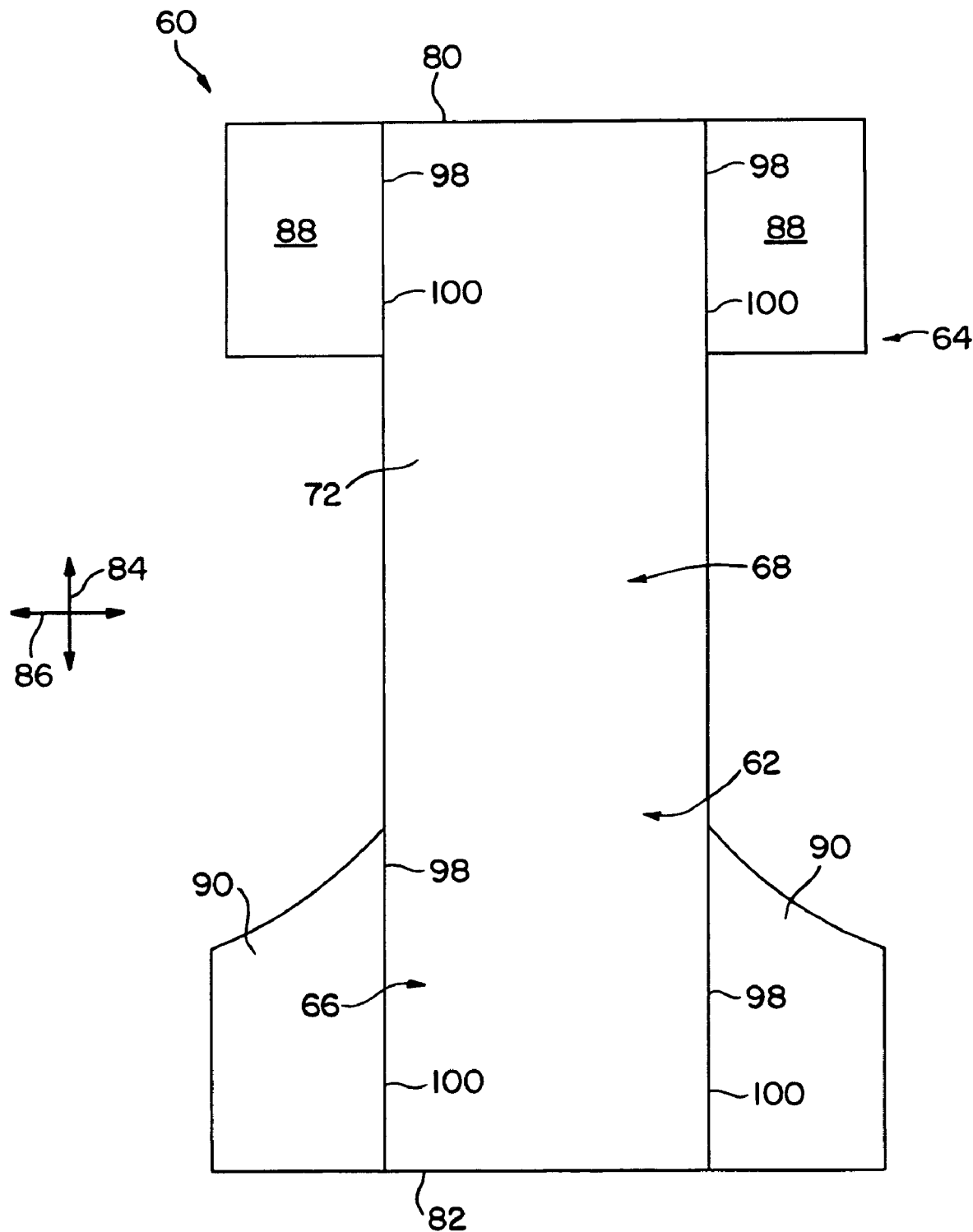
FIG. 3 is a plan view of an unfolded absorbent article similar to the one shown in FIG. 2.
Figure 4:
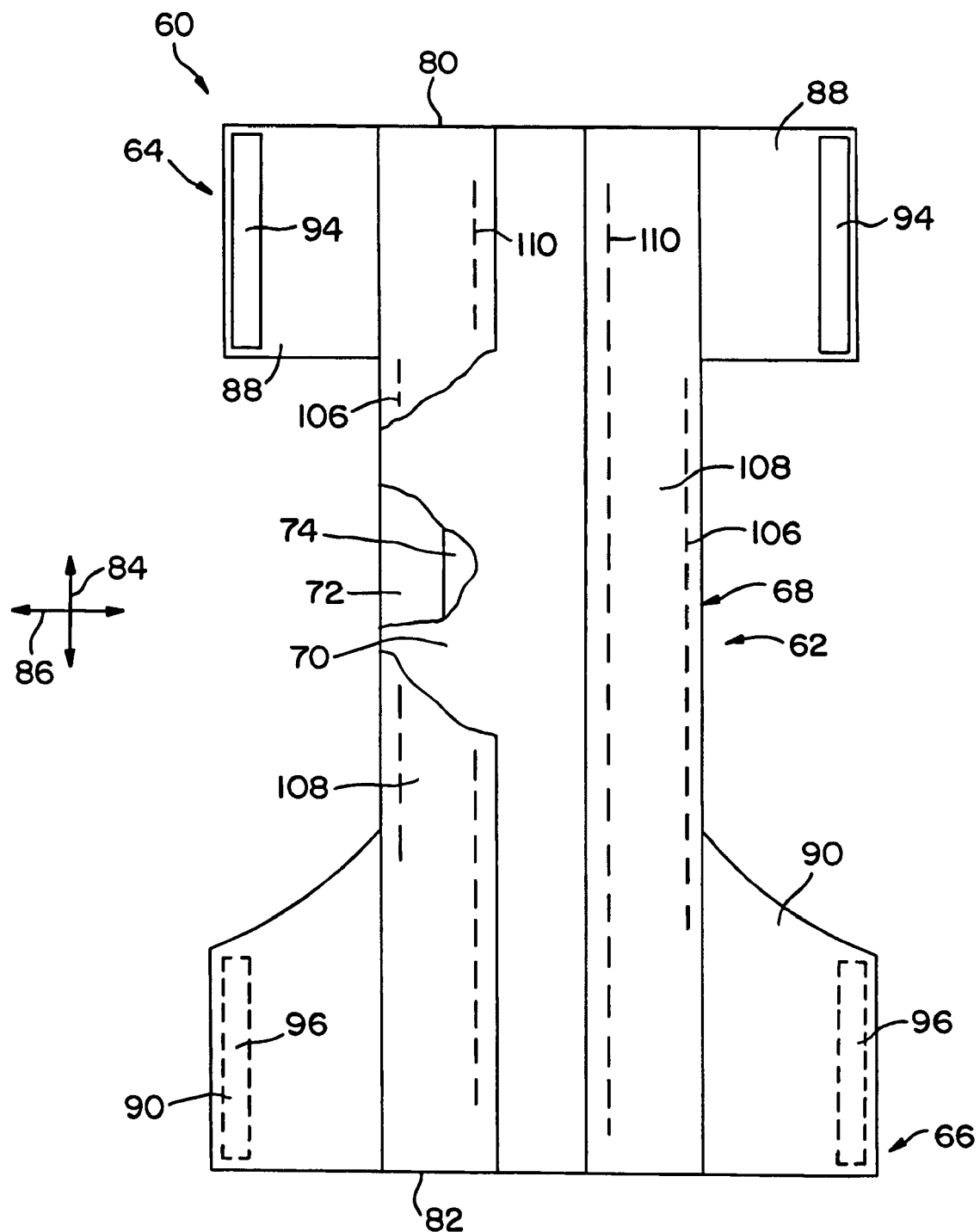
FIG. 4 is a plan view with cutaway portions of the absorbent article shown in FIG. 3.

As shown in further detail in FIGS. 3 and 4, the chassis 62 also defines a pair of longitudinally opposed waist edges which are designated front waist edge 80 and back waist edge 82. The front region 64 is contiguous with the front waist edge 80, and the back region 66 is contiguous with the back waist edge 82. The waist edges 80, 82 are configured to encircle the waist of the wearer when worn and define the waist opening 76. For reference, arrows 84 and 86 depicting the orientation of the longitudinal axis and the transverse axis, respectively, of the absorbent article 60 are illustrated in FIGS. 3 and 4.

The illustrated absorbent chassis 62 includes a pair of transversely opposed front side panels 88, and a pair of transversely opposed back side panels 90. The side panels 88, 90 may be integrally formed with the outer cover 72 and/or the bodyside liner 70 and/or containment flaps of the absorbent, if present, or may include two or more separate elements.

The side panels 88 and 90 desirably include an elastic material capable of stretching in a direction generally parallel to the transverse axis 86 of the absorbent article 60. Suitable elastic materials, as well as processes of incorporating side panels into a training pant, are known to those skilled in the art, and are described, for example, in U.S. Pat. No. 4,940,464 issued Jul. 10, 1990 to Van Gompel et al., which is incorporated herein by reference.

As mentioned, the absorbent article 60 according to the present invention may be refastenable, thereby including a fastening system 92 for securing the training pant above the waist of the wearer (see FIG. 2). The illustrated fastening system 92 may include fastening components 94 that are adapted to refastenably connect to mating fastening components 96. In one embodiment, one surface of each of the fastening components 94 and 96 includes a plurality of engaging elements that project from that surface. The engaging elements of these fastening components 94 are adapted to repeatedly engage and disengage the engaging elements of the mating fastening components 96.

In one particular embodiment, the fastening components 94 each include hook type fasteners and the mating fastening components 96 each include complimentary loop type fasteners. In another particular embodiment, the fastening components 94 each include loop type fasteners and the mating fastening components 96 each include complimentary hook type fasteners.

As noted previously, the illustrated absorbent article 60 has front and back side panels 88 and 90 disposed on each side of the absorbent chassis 62. These transversely opposed front side panels 88 and transversely opposed back side panels 90 can be permanently bonded to the composite structure comprising the absorbent chassis 62 in the respective front and back regions 64 and 66. Additionally, the side panels 88 and 90 can be permanently bonded to one another using suitable bonding means, such as adhesive bonds or ultrasonic bonds, to provide a non-fastenable absorbent article 60. Alternatively, the side panels 88 and 90 can be releaseably attached to one another by a fastening system 92 as described above. More particularly, as shown best in FIG. 3, the front side panels 88 can be permanently bonded to and extend transversely beyond the linear side edges 98 of the composite structure in the front region 64 along attachment lines 100, and the back side panels 90 can be permanently bonded to and extend transversely beyond the linear side edges 98 of the composite structure in the back region 66 along attachment lines 100. The side panels 88 and 90 may be attached using attachment means known to those skilled in the art such as adhesive, thermal or ultrasonic bonding. The side panels 88 and 90 can also be formed as a portion of a component of the composite structure, such as the outer cover 72, containment flaps, if present, or the bodyside liner 70.

Each of the side panels 88 and 90 can include one or more individual, distinct pieces of material. In particular embodiments, for example, each side panel 88 and 90 can include first and second side panel portions that are joined at a seam, with at least one of the portions including an elastomeric material. Still alternatively, each individual side panel 88 and 90 can include a single piece of material which is folded over upon itself along an intermediate fold line (not shown). Desirably, the side panels 88 and 90 include an elastic material capable of stretching in a direction generally parallel to the transverse axis 86 of the absorbent article 60.

To enhance containment and/or absorption of body exudates, the absorbent article 60 may include a front waist elastic member 102, a rear waist elastic member 104, and leg elastic members 106, as are all known to those skilled in the art (see FIG. 4). The waist elastic members 102 and 104 can be operatively joined to the outer cover 72 and/or the bodyside liner 70 along the opposite waist edges 80 and 82, and can extend over part or all of the waist edges. The leg elastic members 106 are desirably operatively joined to the outer cover 72 and/or bodyside liner 70 along opposite side edges of the chassis 62 and positioned in the crotch region 68 of the absorbent article 60.

The waist elastic members 102, 104 and the leg elastic members 106 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and attached to a substrate, attached to a gathered substrate, or attached to a substrate and then elasticized or shrunk, for example with the application of heat; such that elastic constrictive forces are imparted to the substrate. In one particular embodiment, for example, the leg elastic members 106 include a plurality of dry-spun coalesced multifilament spandex elastomeric threads sold under the trade name LYCRA and available from E.I. DuPont de Nemours and Co., Wilmington, Del.

To enhance containment and/or absorption of any body exudates discharged from the wearer, the chassis 62 may include a pair of containment flaps 108 which are configured to provide a barrier to the transverse flow of body exudates. A flap elastic member 110 (see FIG. 4) may be operatively joined with each containment flap 108 in any suitable manner as is well known in the art. The elasticized containment flaps 108 define an unattached edge which assumes an upright, generally perpendicular configuration in at least the crotch region 68 of the absorbent article 60 to form a seal against the wearer's body. The containment flaps 108 can be located along the transversely opposed side edges of the chassis 62, and can extend longitudinally along the entire length of the chassis or may only extend partially along the length of the chassis. Suitable constructions and arrangements for the containment flaps 108 are generally well known to those skilled in the art.

The absorbent articles 60 as shown in FIGS. 1-4 can be made from various materials. The outer cover 72 may be made from a material that is substantially liquid and permeable, and can be elastic, stretchable or nonstretchable. The outer cover 72 can be a single layer of liquid and permeable material, or may include a multi-layered laminate structure in which at least one of the layers is liquid and permeable. For instance, the outer cover 72 can include a liquid permeable outer layer and a liquid and permeable inner layer that are suitably joined together by a laminate adhesive.

For example, in one embodiment, the liquid permeable outer layer may be a spunbond polypropylene nonwoven web. The spunbond web may have, for instance, a basis weight of from about 15 gsm to about 25 gsm.

The inner layer, on the other hand, can be both liquid and vapor impermeable, or can be liquid impermeable and vapor permeable. The inner layer is desirably manufactured from a thin plastic film, although other flexible liquid impermeable materials may also be used. The inner layer prevents waste material from wetting articles such as bedsheets and clothing, as well as the wearer and caregiver. A suitable liquid impermeable film may be a polyethylene film having a thickness of about 0.2 mm.

A suitable breathable material that may be used as the inner layer is a microporous polymer film or a nonwoven fabric that has been coated or otherwise treated to impart a desired level of liquid impermeability. Other "non-breathable" elastic films that may be used as the inner layer include films made from block copolymers, such as styrene-ethylene-butylene-styrene or styrene-isoprene-styrene block copolymers.

As described above, the absorbent assembly is positioned in between the outer cover and a liquid permeable bodyside liner 70. The bodyside liner 70 is desirably compliant, soft feeling, and non-irritating to the wearer's skin. The bodyside liner 70 can be manufactured from a wide variety of web materials, such as synthetic fibers, natural fibers, a combination of natural and synthetic fibers, porous foams, reticulated foams, appertured plastic films, or the like. Various woven and nonwoven fabrics can be used for the bodyside liner 70. For example, the bodyside liner can be made from a melt-blown or spunbonded web of polyolefin fibers. The bodyside liner can also be a bonded-carded web composed of natural and/or synthetic fibers.

A suitable liquid permeable bodyside liner 70 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber. In this particular embodiment, the polypropylene forms the core and the polyethylene forms the sheath of the fiber. Other fiber orientations, however, are possible.

The various processes that may be used to form absorbent structures in accordance with the present invention will now be described. For instance, referring to FIG. 8, one exemplary process and system generally 120 for forming absorbent structures, such as absorbent structure 10 as shown in FIG. 5, is illustrated. In this embodiment, a continuous strip of an air formed absorbent fibrous web 140 is produced and manipulated into individual absorbent structures or pads 10. It should be understood, however, that the fibrous web may be made according to various other processes instead of an air forming process.

As shown, a selected fibrous material is introduced into the system as air-entrained fibers in a stream flowing in the direction toward a porous forming surface 128. The fibers, for instance, may suitably be derived from a batt of cellulosic fibers, such as wood pulp fibers, or other source of natural or synthetic fibers, which has been subjected to a fiberization treatment. For example, a hammer mill or other conventional fiberizer may be employed. Particles or fibers of superabsorbent material may also be introduced into a forming chamber 122 by employing conventional mechanisms, such as pipes, channels, spreaders, nozzles and the like.

The fibers and particles, in this embodiment, may be entrained in any suitable gaseous medium. References herein to air as being the entraining medium should be understood to be a general reference which encompasses any other operative entrainment gas.

The stream of air-entrained fibers and particles can pass through the forming chamber 122 to a forming drum system generally 124. The forming chamber 122 can serve to direct and concentrate the air-entrained fibers and particles, and to provide a desired velocity profile in the air-entrained stream of fibers and particles.

As shown, the forming surface 128 of the forming drum system 124 is mounted on a rotatable forming drum 126. The forming drum 126 is rotatable in a selected direction of rotation, and can be rotated by employing a drum drive shaft that is operatively joined to any suitable drive mechanism (not shown). For example, the drive mechanism can include an electric or other motor which is directly or indirectly coupled to the drive shaft. While the shown arrangement provides a forming drum that is arranged to rotate in a counter-clockwise direction, it should be readily apparent that the forming drum may alternatively be arranged to rotate in a clockwise direction.

The forming drum 126 can provide a lay down zone 130 which is positioned within the forming chamber 122 and provides a vacuum lay down zone of the foraminous forming surface 128. This vacuum lay down zone 130 constitutes a circumferential, cylindrical surface portion of the rotatable drum 126. An operative pressure differential is imposed on the surface of the vacuum lay down zone under the action of a conventional vacuum generating mechanism, such as a vacuum pump, an exhaust blower or other suitable mechanism which can provide a relatively lower pressure under the forming surface 128. The vacuum mechanism can operatively withdraw air from the arcuate segment of the forming drum 126 associated with the vacuum lay down surface through an air discharge duct 138. The foraminous forming surface 128 can include a series of forming sections which are distributed circumferentially along the periphery of the forming drum 126. In desired arrangements, the forming sections can provide a selected repeat pattern that is formed in the fibrous web 140. The repeat pattern can correspond to a desired shape of an individual absorbent pad that is intended for assembly or other placement in a desired absorbent article.

Suitable forming drum systems for producing air formed fibrous webs are well known in the art. For example, U.S. Pat. Nos. 4,666,647, 4,761,258, 4,927,582, U.S. Patent Application Publication No. 2003/0042660 and U.S. Pat. No. 6,330,735 all disclose air forming systems and are all incorporated herein by reference.

Thus, under the influence of the vacuum mechanism, a conveying air stream is drawn through the foraminous forming surface 128 into the interior of the forming drum 126, and is subsequently passed out of the drum through the discharge duct 138. As the air-entrained fibers and particles impinge on the foraminous forming surface 128, the air component thereof is passed through the forming surface and the fibers-particles component is retained on the forming surface to form a non-woven fibrous web 140 thereon. Subsequently, with rotation of the forming drum 126, the formed web 140 can be removed from the forming surface by the weight of the fibrous web 140, by centrifugal force, and by a positive pressure produced, for example, by a pressurized air flow through a blow-off zone 142 and onto a transfer fabric 143. The pressurized air exerts a force directed outwardly through the forming surface. In another embodiment, instead of or in addition to using any of the above web removal methods, a suction device may be placed below the transfer fabric 143 for also assisting in the transfer of the formed web. Additionally, the distinctive configurations of the forming surface and associated components, can produce a fibrous web 140 which can be more readily removed from the forming drum 126.

The forming drum 126 can be rotatable about a series of stationary baffles which can present to the foraminous forming surface 128, a plurality of differential pressure zones. The pressure differentials imposed on the foraminous forming surface 128 can be produced by any conventional, vacuum generating mechanism, such as an exhaust fan, which is connected to the air discharge duct 138 and is operatively joined to the forming drum structure by employing a conventional coupling mechanism. The interior space of the forming drum 126 can include a high vacuum forming zone which is in the general form of an arcuate segment that is operatively located at the portion of the forming surface 128 that is positioned within the forming chamber 122. In the shown configuration, the high vacuum forming zone is located generally adjacent to the forming chamber.

The forming surface 128 can be provided along the outer, cylindrical surface of the forming drum 126, and the forming surface can include a plurality of contoured forming surface portions that are circumferentially spaced apart along the outer surface of the forming drum. In operation, the airlaid fibrous web 140 can be formed from the stream of air-entrained fibers as the entrainment gas flows through the openings in the foraminous forming surface 128 and into the rotating forming drum 126.

Figure 8:
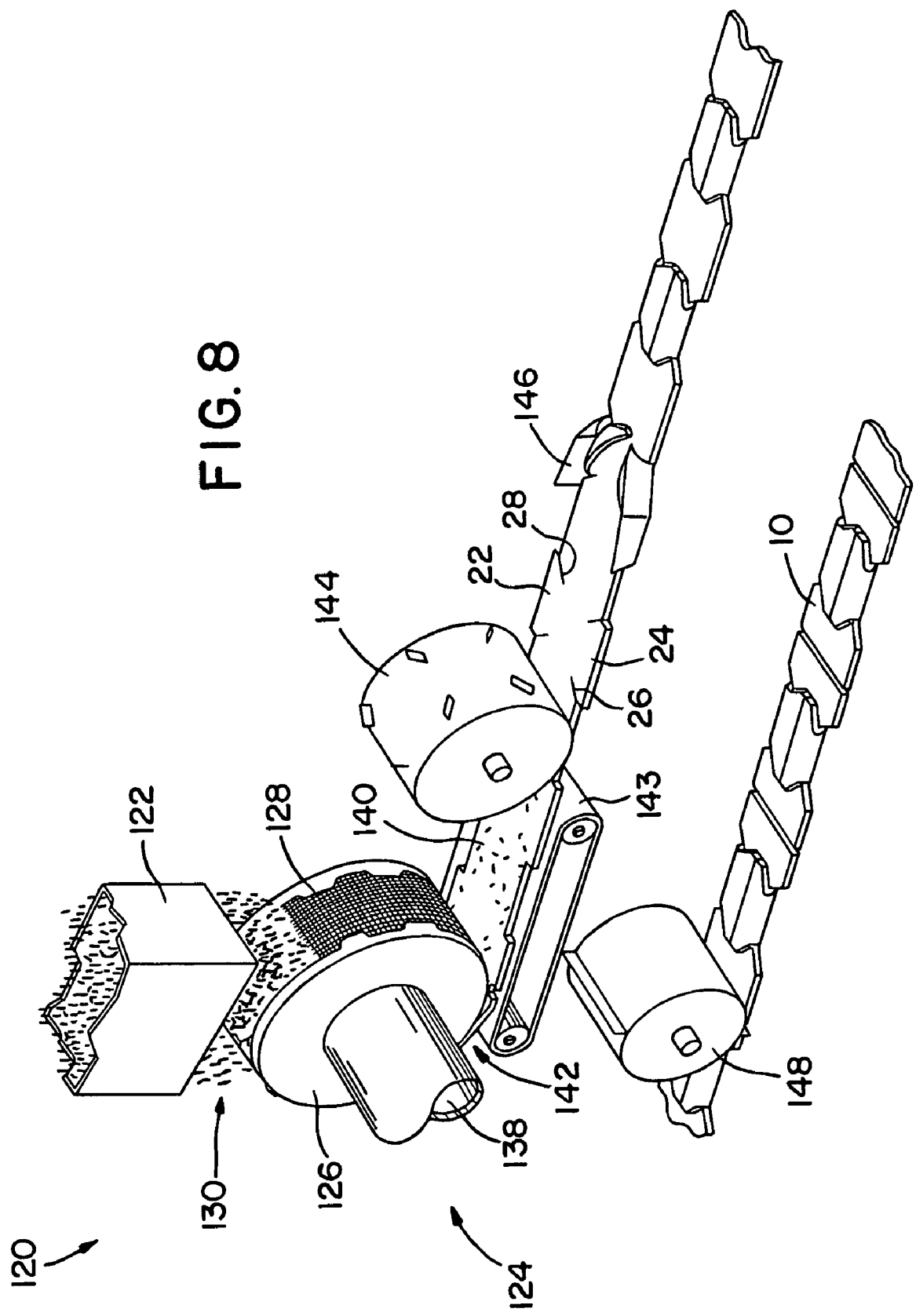
FIG. 8 is a perspective view of a process for forming the absorbent structure illustrated in FIG. 5.

As shown in FIG. 8, the shape of the forming surface 128 produces the continuous strip of absorbent web material 140 that is comprised of a succession of absorbent structures 10. Each absorbent structure is formed with lateral flaps 22 and 24.

After the fibrous web 140 is formed, the web is fed to a cutting device 144. The cutting device 144 forms the front slits 26 and the rear slits 28 into each absorbent structure 10. In this embodiment, the cutting device 144 comprises a roll containing a plurality of cutting blades. It should be understood, however, that any suitable cutting device may be used. For instance, a water cutting device may be used, a laser beam cutting device may be used or a large stamp that moves up and down may be used.

From the cutting device 144, the web of material 140 is fed to a folding device 146. In the embodiment shown, the folding device comprises a pair of stationary folding blades that fold the lateral flaps 22 and 24 onto the absorbent web 140. As described above, since the lateral flaps 22 and 24 form the widest portion of the web material 140, the flaps are easily engaged by the stationary folding device 146. It should be understood, however, that any suitable folding device may be used in the process of the present invention. The folding device, for instance, may have moveable parts that assist in folding the lateral flaps. In one particular embodiment, for instance, the folding device may include vibrating blades.

Figure 9:
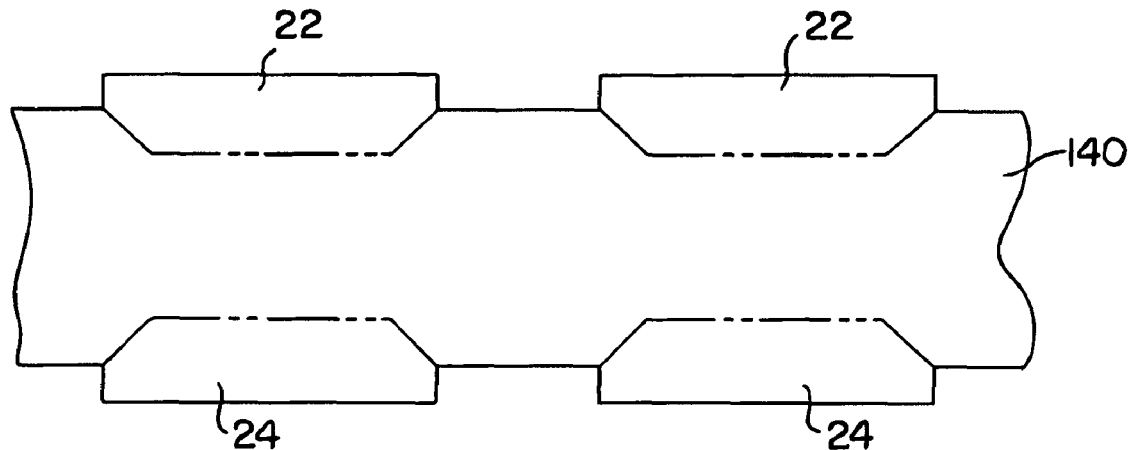
FIGS. 9-11 are plan views of a strip of web material being sequentially formed into a plurality of absorbent structures as shown in FIG. 5.
Figure 10:
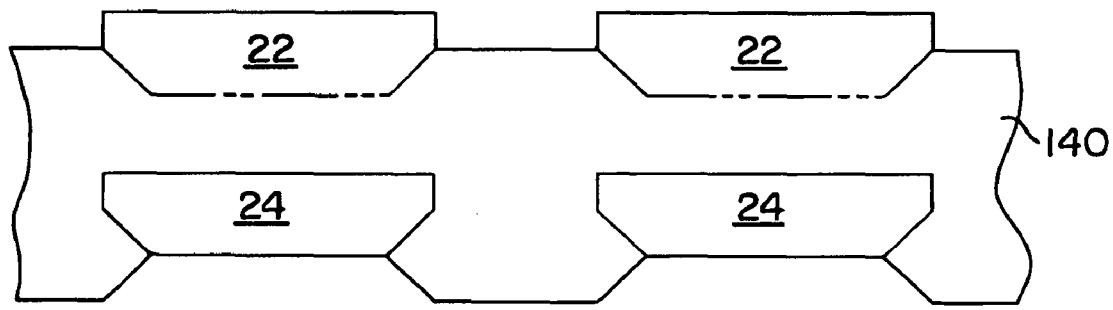
Figure 11:
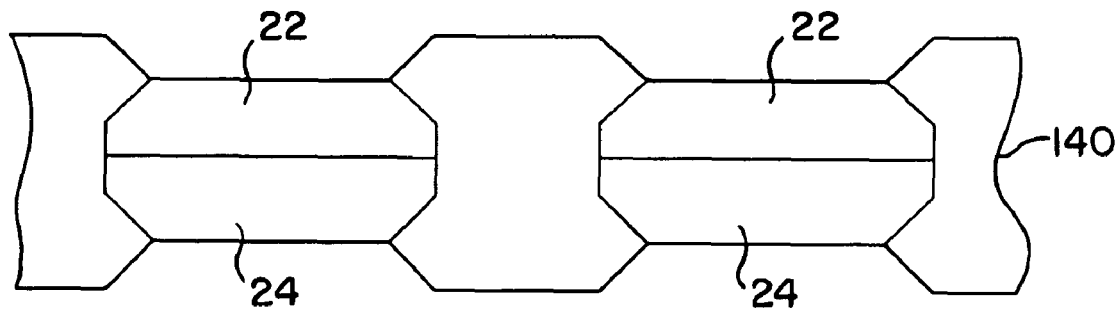

Referring to FIGS. 9-11, the continuous strip of material 140 is shown wherein the lateral flaps 24 are first folded onto the web material followed by the lateral flaps 22.

After the lateral flaps 22 and 24 have been folded, the continuous strip of material is then fed to a second cutting device 148. The cutting device 148 forms a cross machine direction cut through the absorbent web material to form individual absorbent pads 10. The cutting device 148 may be the same or different from the cutting device 144. Once each individual absorbent structure or pad 10 is formed, the pads may then be incorporated into an absorbent article, such as the garment 60 as shown in FIG. 1.

As shown in FIG. 8, the absorbent structures 10 are formed from a fibrous web that has a substantially uniform basis weight. By folding the lateral flaps 22 and 24, an absorbent structure 10 may be formed with a differential basis weight without having to use a 3-dimensional forming surface 128 and without having to scarf the fibrous web after it is formed.

The basis weight of the fibrous web 140 may vary dramatically depending upon the particular circumstances and the materials used to form the web. For many applications, for instance, the basis weight of the web may vary from about 100 gsm to about 1000 gsm.

Figure 15:
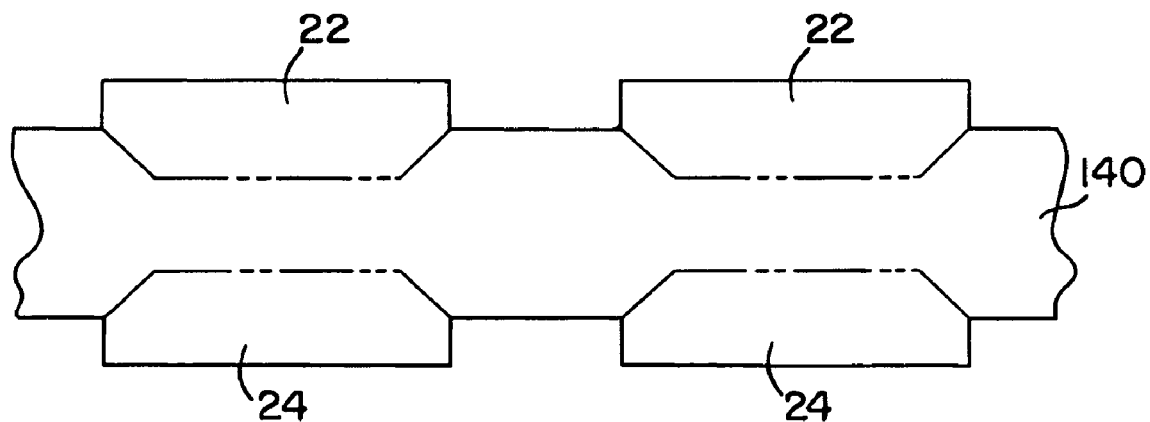
FIGS. 15-17 are successive plan views of a strip of web material being formed into a plurality of absorbent structures as shown in FIG. 12.
Figure 16:
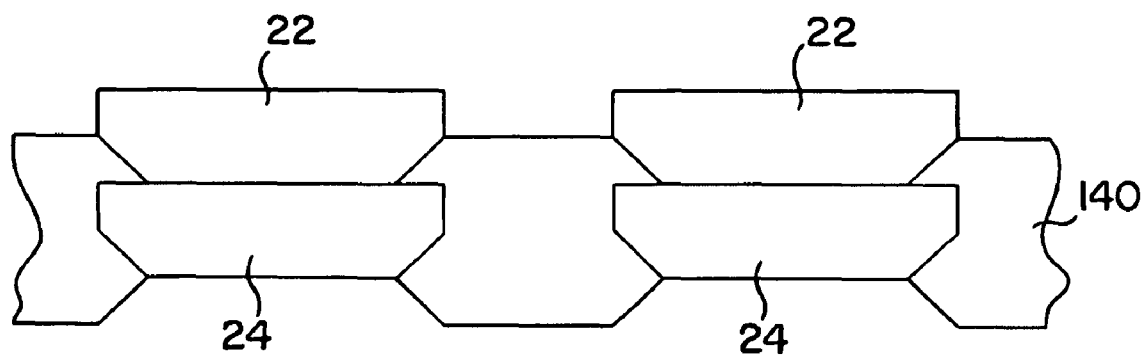
Figure 17:
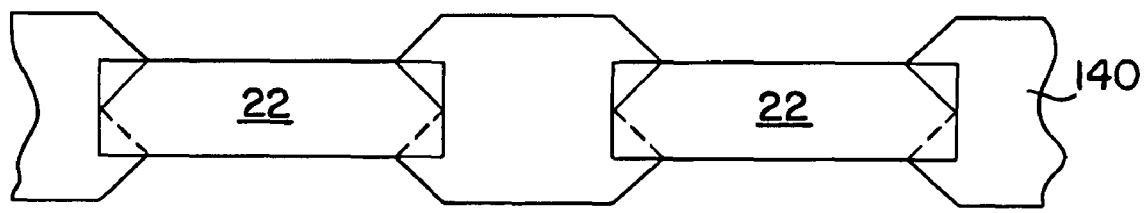

Referring to FIGS. 15-17, the absorbent structure generally 30 as shown in FIG. 12 may also be formed from a continuous strip of material 140. FIGS. 15-17 illustrate the lateral flaps 22 and 24 being folded onto the absorbent web material. The succession of absorbent structures may then be cut in the cross machine direction to form individual pads.

Figure 21:
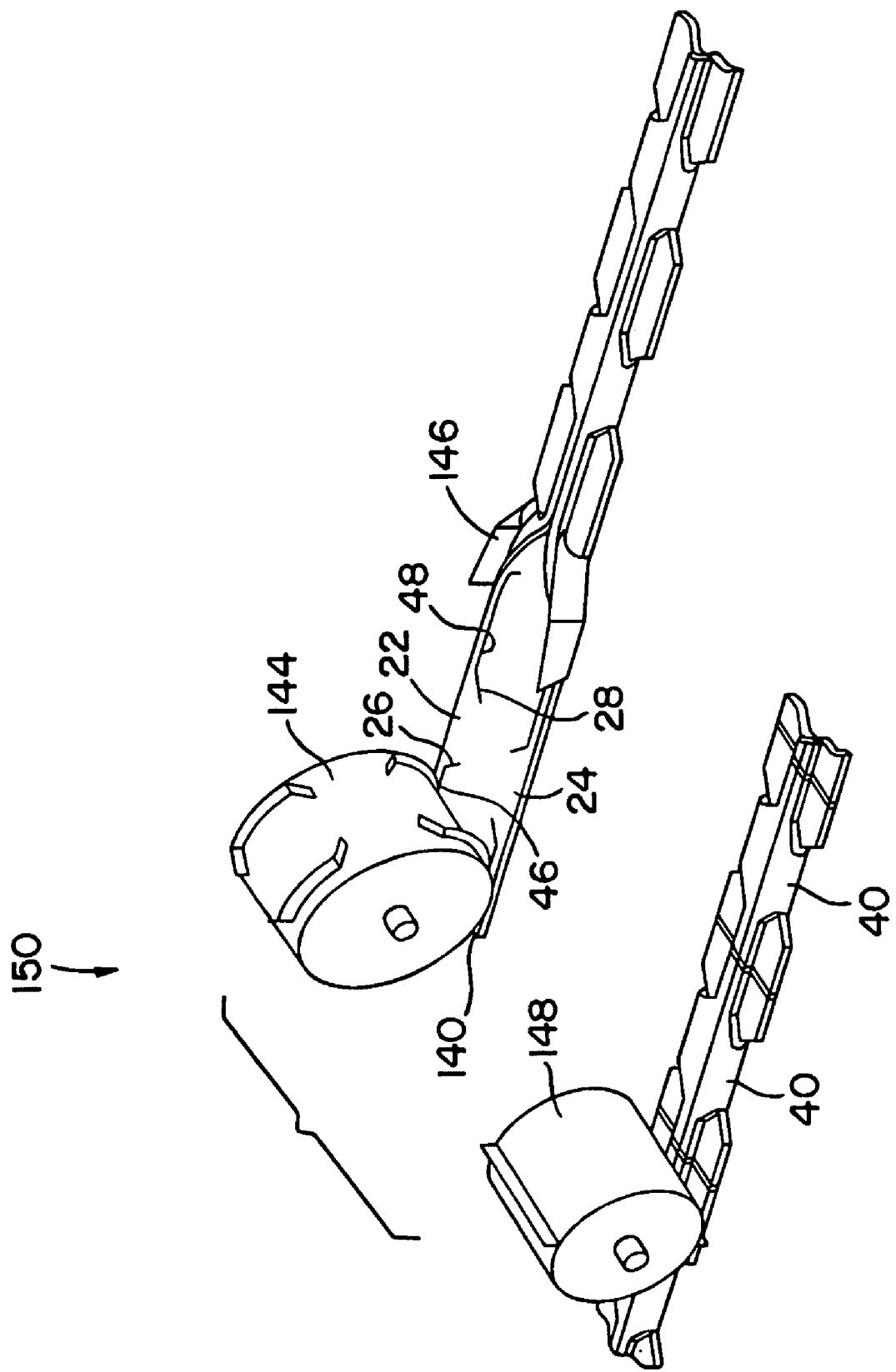
FIG. 21 is a perspective view of one embodiment of a process for forming the absorbent structure shown in FIG. 18.

Referring to FIG. 21, another exemplary process or system 150 made in accordance with the present invention for forming absorbent structures, such as an absorbent structure 40 as shown in FIG. 18, is illustrated. In this embodiment, the continuous strip of web material is preformed in an offline process and fed to a cutting device 144. The web material 140 may be formed according to an air formed process, a coform process, a meltspun process, a fiber carding process, a wet lay process, or by any other suitable means. Further, it should be also understood that the continuous strip of web material may be cut by the cutting device 144 and then wound into a roll for later processing.

As shown, the cutting device 144 forms slits 26, 46, 28, and 48 into the absorbent web. Since the lateral flaps 22 and 24 extend the entire length of each absorbent structure, in this embodiment, the lateral flaps 22 and 24 form a continuous ribbon along the entire length of the strip of web material 140. By forming a continuous ribbon of material that also forms the widest portion of the absorbent web 140, it is a relatively simple exercise for the folding device 146 to fold the lateral flaps onto the web material.

After the lateral flaps 22 and 24 have been folded, the web material 140 is fed to a second cutting device 148 which cuts the strip of web material into individual absorbent structures 40. The individual absorbent structures 40 may be directly fed into a process for forming absorbent garments.

Figure 22:
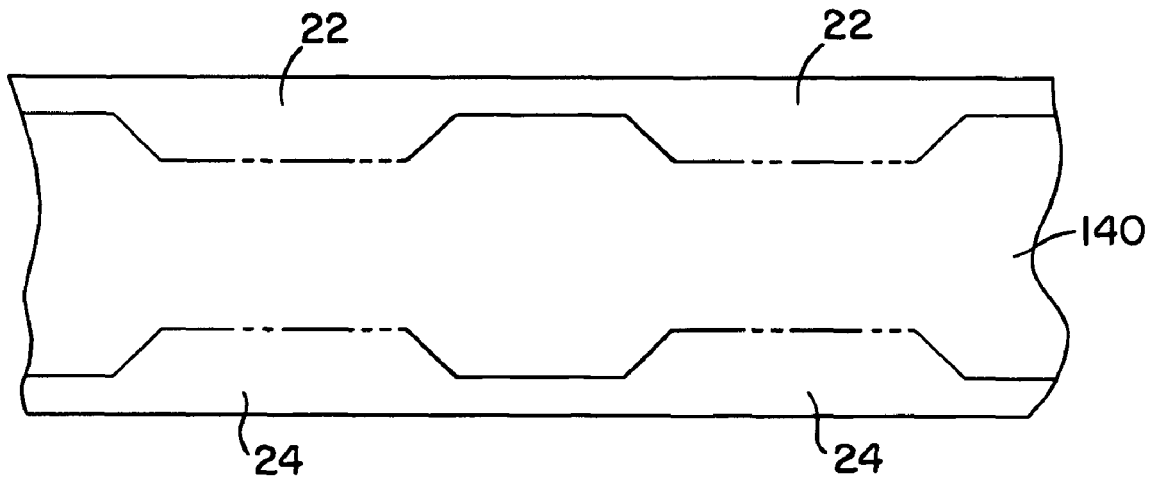
FIGS. 22-24 are successive plan views of a strip of web material being formed into a plurality of absorbent structures as shown in FIG. 18.
Figure 23:
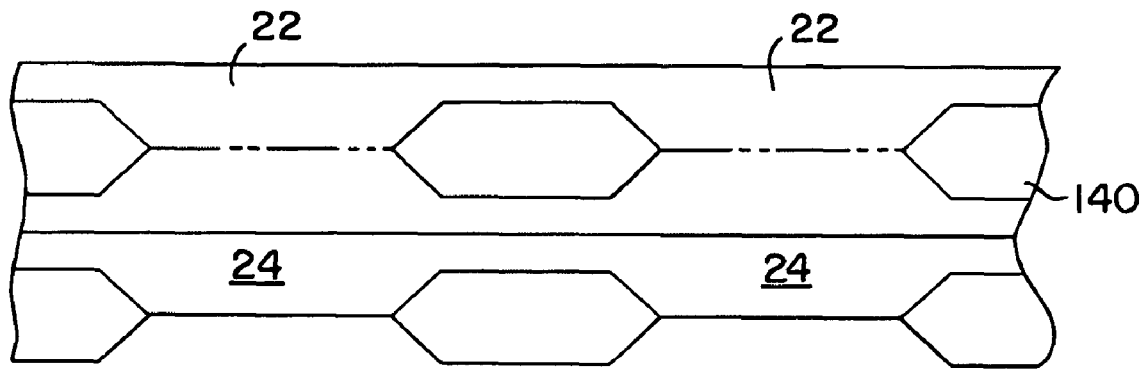
Figure 24:
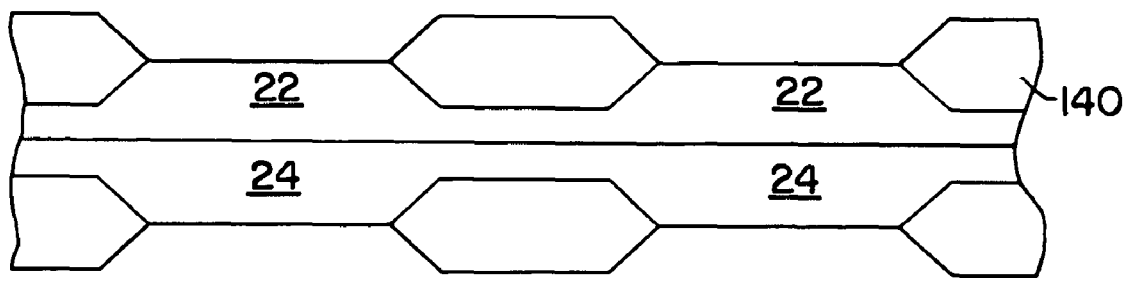
Figure 28:
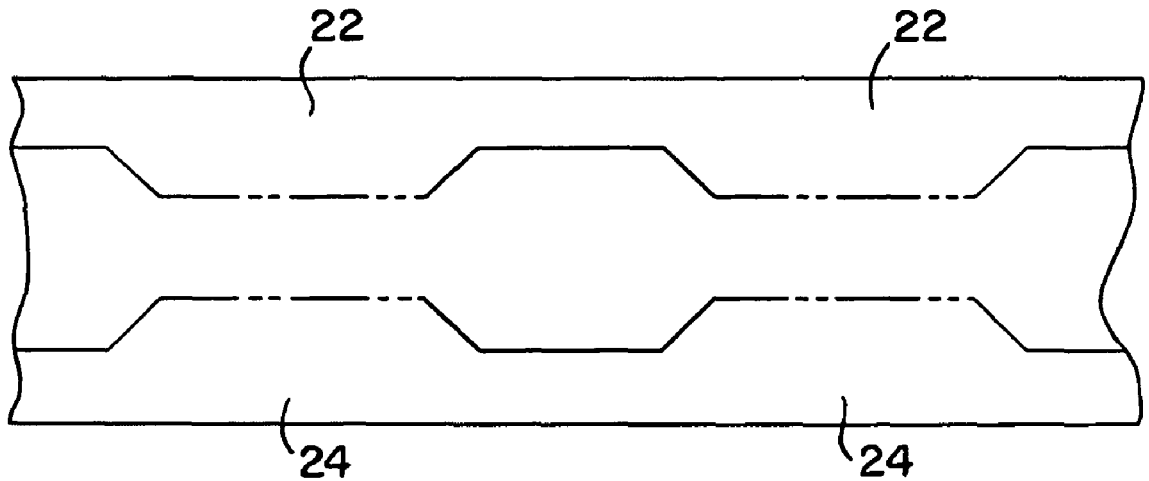
FIGS. 28-30 are successive plan views of a strip of web material being formed into a plurality of absorbent structures as shown in FIG. 25.
Figure 29:
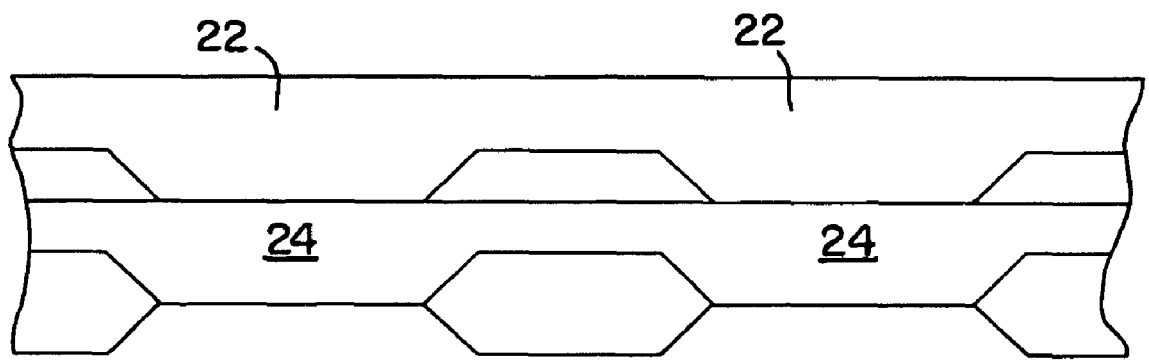
Figure 30:
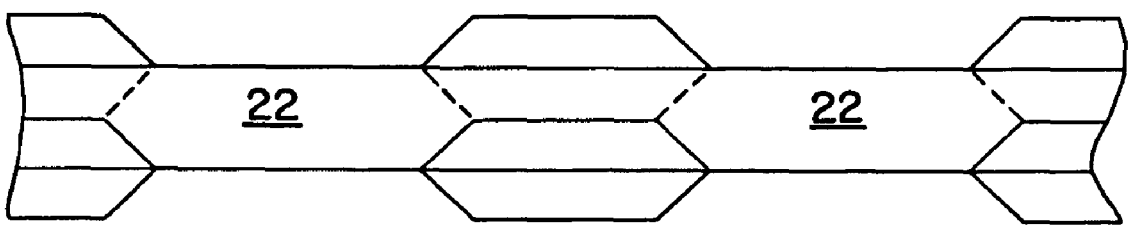

Referring to FIGS. 22-24, the folding of flaps 22 and 24 on the absorbent web material 140 is shown in a step-by-step manner. Referring to FIGS. 28-30, the folding of the lateral flaps 22 and 24 of the blank 56 as shown in FIG. 27 is also illustrated.

In various embodiments, other processing steps may occur on the absorbent fibrous web 140 as the individual absorbent structures are being formed. For instance, in one embodiment, the fibrous web may be densified by being fed through a debulking device. The debulking device may densify the entire web or only the lateral flaps of the web. In other embodiments, score lines may also be formed into the web in order to assist in folding the lateral flaps over onto the middle portion of the web.

In still other embodiments, an adhesive may be sprayed onto the web in order to secure the lateral flaps to the web. In general, any suitable adhesive may be used.

Once the absorbent structures are formed, the absorbent structures may then be fed to a processing line for incorporating the structures into an absorbent garment, such as any of the products shown in FIGS. 1-4.

Figure 31:
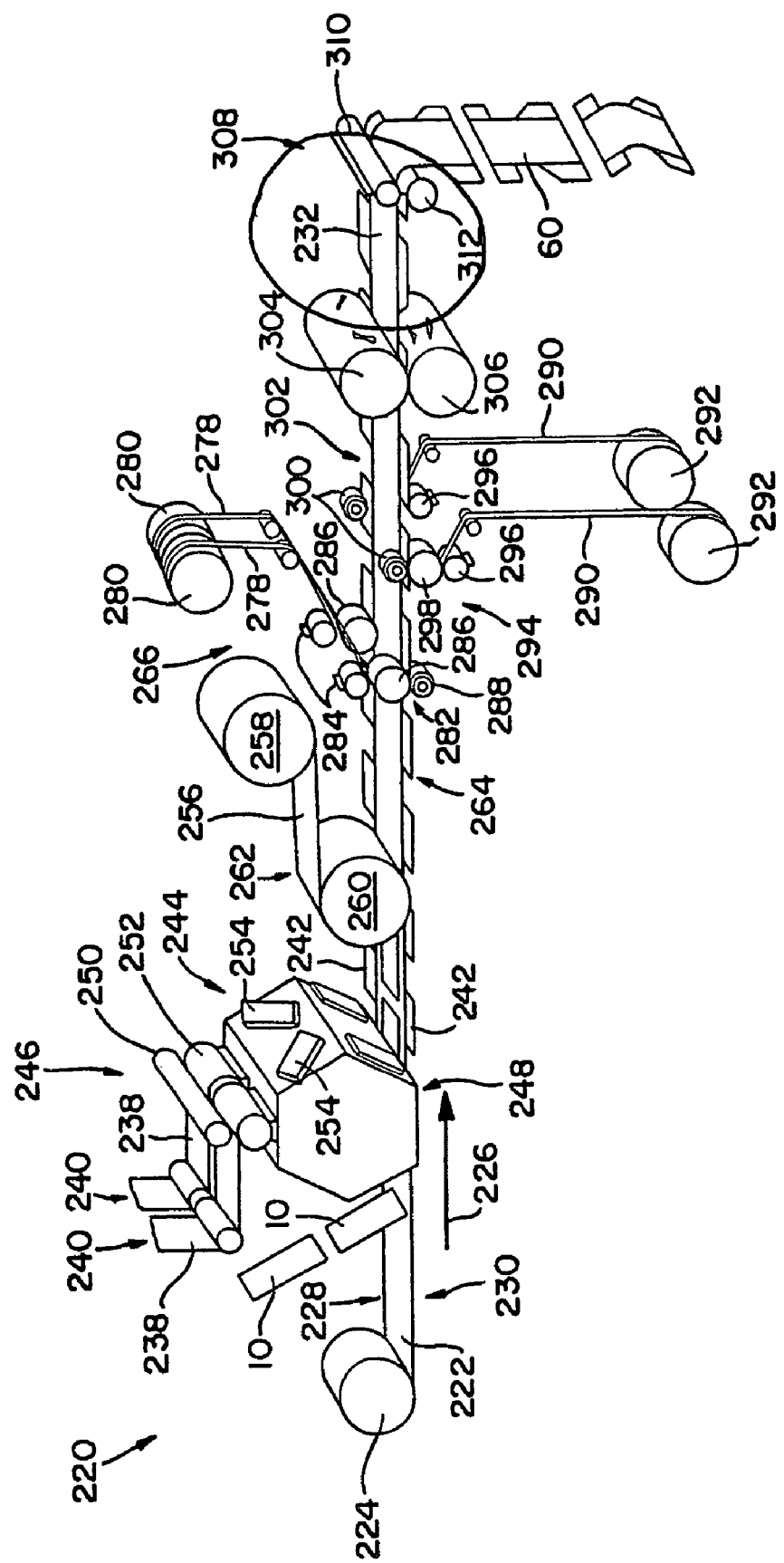
FIG. 31 is a perspective view of one embodiment of a process and system for forming absorbent products in accordance with the present invention.

Referring now to FIG. 31, an exemplary embodiment of an assembly section 220 for making a continuous stream of partially assembled, discrete pants or garments 60 is illustrated. The specific equipment and processes used in the assembly section 220 can vary greatly depending on the specific type of garment being manufactured. The particular process and apparatus described in relation to FIG. 31 is specifically adapted to manufacture absorbent articles 60 pull-on style of the type illustrated in FIGS. 1 through 4.

The various components of the garment 60 can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIG. 31.

A continuous supply of material 222 used to form the bodyside liner 70 is provided from a supply source 224. The supply source 224 can include for example a pair of spindles, a festoon assembly, and optionally a dancer roll (not shown) for providing bodyside liner material 222 at a desired speed and tension.

Various components can be disposed on and/or bonded to the bodyside liner material 222 as the material travels in a machine direction identified by arrow 226. In particular, a surge layer can be provided at an application station 228 and disposed on and/or bonded to the bodyside liner material 222. The surge layer can include either a continuous web or discrete sheets. Additionally, a containment flap module 230 can be provided downstream of the supply source 224 for attaching pre-assembled containment flaps to the bodyside liner material 222. As various components are added in the assembly section 220, a continuously moving product assemblage 232 is formed. The product assemblage 232 will be cut downstream to form the partially assembled, discrete garments 60.

A plurality of absorbent structures 10 are provided from a suitable supply source. The supply source can be, for instance, the air forming system and process as shown in FIG. 8 or as shown in FIG. 21.

Assembly section 220 can include a device to apply side panels. For example, continuous webs of material 238 used to form the side panels 88 and 90 can be provided from suitable supply sources 240. The supply sources 240 can include one or more unwind mechanisms. The side panel material 238 can be cut into individual strips 242 and positioned partially on the bodyside liner material 222 using an applicator device 244. In the cross machine direction, the individual strips 242 desirably extend laterally outward from the bodyside liner material 122 and overlap the bodyside liner material to permit bonding of the strips to the bodyside liner and/or the containment flap material. Bonding may be accomplished using adhesives, as is well known in the art, or by any other bonding means. In the machine direction 226, the position of the strips 242 can be registered relative to the absorbent assemblies 234 so that the product assemblage 232 can be cut between the absorbent assemblies with each strip 242 of side panel material 238 forming both a front side panel 88 and a back side panel 90 of consecutive garments 60.

One suitable applicator device 244 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 244 can include a cutting assembly 246 and a rotatable transfer roll 248. The cutting assembly 246 employs a rotatable knife roll 250 and a rotatable vacuum anvil roll 252 to cut individual strips 242 from the continuous side panel material 238. The strips 242 cut by a blade on the knife roll 250 can be maintained on the anvil roll 252 by vacuum and transferred to the transfer roll 248.

The rotatable transfer roll 248 can include a plurality of rotatable vacuum pucks 254. The vacuum pucks 254 receive the strips 242 of material 238 from the cutting assembly 246 and rotate and transfer the strips to the continuously moving bodyside liner material 222. When the strips 242 are positioned as desired relative to the bodyside liner material 222, the strips are released from the pucks 254 by extinguishing the vacuum in the pucks. The pucks 254 can continue to rotate toward the cutting assembly 246 to receive other strips.

Alternative configurations for attaching the side panel material 238 exist. For instance, the material 238 used to form the side panels can be provided in continuous form and contour cut to form leg openings 78. Still alternatively, the side panels 88 and 90 of the pant 60 can be provided by portions of the bodyside liner 70 and/or outer cover 72. It should be noted that the side panel application processes just described are exemplary only, and that the process can vary greatly depending on the physical characteristics of the material and the nature of the process.

A continuous supply of material 256 used to form the outer cover 72 can be provided from a supply roll 258 or other suitable source. As the material is unwound, the outer cover material 256 can be married with the bodyside liner material 222 such as by use of a laminator roll 260. The absorbent assemblies 234 are thereby sandwiched between the continuous materials 222 and 256. The inward portions of the strips 242 of side panel material 238 can also be disposed between the bodyside liner material 222 and the outer cover material 256. Various components such as leg elastics 106 or waist elastics 102 and 104 can be bonded to the outer cover material 256 at an application station 262 prior to uniting the bodyside liner and outer cover materials 222 and 256. Alternatively, leg elastics or waist elastics can be initially bonded to the bodyside liner material 222 or another material.

The outer cover 256 can be joined to the liner-side panel composite using any means known to those of skill in the art. Where an adhesive is used, the adhesive can be applied on or prior to laminator roll 260. Alternatively, bonding devices such as ultrasonic or thermal bonders can be employed as part of the laminator roll 260 or at a downstream location 264 to bond the bodyside liner material 222, side panel material 238 and outer cover material 256.

The assembly section 220 can include apparatus to provide/apply a fastening system to the garment 60. For example, the continuously moving product assemblage next advances to a fastener application station 266 where fastening components 94 and 96 are bonded to the strips 242 of side panel material 238. The location of the fastening components on the composite is a function in part of the configuration of the assembly section 220. The illustrated assembly section 220 is configured so that the upwardly facing surface of the product assemblage 232 will become the outer surface of the pant 60 and the downwardly facing surface will become the inner surface. Moreover, the illustrated assembly section 220 is configured to produce partially assembled garments 60 having the front waist region 64 of a leading garment connected to the back waist region 66 of a trailing garment. The process could alternatively employ any combination of different orientations. For example, the upwardly facing surface of the product assemblage could form the inner surface of finished garments. Additionally or alternatively, the back waist region 66 of a leading garment can be connected to the front waist region 64 of the trailing garment, or the garments can be arranged in a front-to-front/back-to-back relationship. Still alternatively, the assembly section 220 can be constructed as a cross-machine direction process wherein the longitudinal axis of each garment could be perpendicular to the machine direction 226 during part or all of the assembly process.

Continuous webs of a fastener material 278 used to form the fastening components 96 (FIGS. 2 and 4) can be provided from supply rolls 280 or other suitable sources. The fastener materials 278 can be cut into individual fasteners 96 by cutting assemblies 282 or other suitable devices. The illustrated cutting assemblies 282 include rotatable knife rolls 284, rotatable vacuum anvil rolls 286, and rotatable backing rolls 288. The continuous fastener materials 278 can be cut by blades on the knife rolls 284, maintained on the anvil rolls 286 by vacuum, and disposed on the top surfaces of the strips 242 of side panel material 238.

Similarly, continuous webs of a fastener material 290 used to form the fastening components 94, shown in FIGS. 2 and 4, can be provided from supply rolls 292 or other suitable sources. The first fastener materials 290 can be cut into individual first fasteners 94 by cutting assemblies 294 or other suitable devices.

Alternatively, a component of the garment 60 may serve as the fastening components, in which case the fastener application station 266 or the cutting assemblies 294 may not be needed. The illustrated cutting assemblies 294 include rotatable knife rolls 296, rotatable vacuum anvil rolls 298, and rotatable backing rolls 300. The continuous fastener materials 290 can be cut by blades on the knife rolls 296, maintained on the anvil rolls 298 by vacuum, and disposed on the undersides of the strips 242 of side panel material 238.

Other arrangements can be used to attach the fastening components 94 and 96. For example, the fastening components can be applied to the side panel material 238 prior to uniting the side panel material with the bodyside liner material 222 and/or the outer cover material 256; the fastening components can be applied to the bodyside liner material 222 and/or outer cover material 256, whether separate side panels are used or not; portions of other components such as the bodyside liner and/or outer cover can form one or more of the fastening components; the separate side panels or integral side panels can themselves form one or more of the fastening components; the fastening components can be attached as pre-engaged composites; or the like.

After the fastening components are disposed on the strips 242 of side panel material 238, bonding devices 302 such as ultrasonic bonders can be employed to bond the fastening components to the strips. For example, the strips 242 can be transported between a rotary ultrasonic horn and an anvil roll, which devices are positioned on each side of the process at the cross machine direction location of the fastening components 94 and 96. Particular ultrasonic bond patterns including individual, circular bonds which are compatible with mechanical fastening materials are disclosed in U.S. Pat. No. 5,660,666 issued Aug. 26, 1997 to Dilnik et al., which is incorporated herein by reference. Efficient arrangements for attaching the fastening components with nonadhesive bonding devices are further described in U.S. Pat. No. 6,562,167, filed on May 15, 2001 by J. D. Coenen et al. and titled "Methods For Making Garments With Fastening Components", which is incorporated herein by reference. For secure attachment, it may be desirable to attach the fastening components with both adhesive and thermal bonds. Suitable attachment adhesives are available from commercial vendors such as Findley Adhesive, Inc., Wauwatosa, Wis. U.S.A.

In particular embodiments, the bonding devices 302 can provide timed, non-uniform bonding of the fastening components to the side panel material 238. The degree of bonding, such as the number of bonds per unit area or the bond strength per unit area, can be greater in certain target areas compared to non-target areas. Enhanced bonding in target areas can be beneficial particularly near the waist and leg openings to reduce delamination of the fastening components from the side panel material 238. Thus, the bonding devices 302 can be adapted to create relatively more bonds or stronger bonds between the fastening components and the side panel material 238 when the side panel material 238 reaches a particular machine direction 226 location. In one particular embodiment, the target areas correspond to portions of the fastening components 94 and 96 near the waist edges 80 and 82. The bonding devices 302 can be registered to provide a relatively higher degree of bonding which begins while disposed on one fastening component, continues through the region where the product assemblage 232 will subsequently be cut, and ends after being disposed on another fastening component. Alternatively, the bonding devices 302 can destroy engaging elements of the fastening components in the target areas, so that the fastening components will be less able to aggressively attach to one another in the target areas.

The strips 242 of side panel material 238 can be trimmed if desired, for example to provide angled and/or curved leg end edges in the back waist region. To this end, the assembly section 220 can include a die cutting roll 304 and a backing roll 306. In the illustrated embodiment, a portion of each strip 242 is trimmed from a trailing edge in order to form the angled and/or curved leg end edges in the back waist region.

The method and apparatus to this point provides a continuous web of interconnected and partially assembled pants moving in the direction indicated by arrow 226. This continuously moving product assemblage 232 is passed through a cutter 308 which selectively cuts the web into discrete, partially assembled garments 60. Such cutters 308 are generally known to those skilled in the art and can include, for example, the combination of a cutting roll 310 and an anvil roll 312 through which the web travels. The anvil roll 312 can include a hardened steel rotating roll while the cutting roll 310 can include one or more flexible hardened steel blades clamped onto another rotating roll. The pinching force between the blade on the cutting roll 310 and the anvil roll 312 creates the cut. The cutting roll 310 can have one or more blades depending upon the desired distance between the cuts. The cutter 308 can further be configured to provide a spacing between the individual cut pieces after they are cut. Such a spacing can be provided by transferring the cut pieces away from the cutter at a higher speed than the speed at which the web is provided to the cutter.

The discrete garments 60 can then be folded and packaged as desired.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
   an outer cover material;
   a liner; and
   an absorbent structure positioned between the outer cover material and the liner, the absorbent structure including a front portion, a rear portion, and a middle portion, the middle portion positioned between the front portion and the rear portion, the middle portion being narrower than the front portion, the front portion extending from a front edge of the absorbent structure to the narrower middle portion, the front portion defining an outermost lateral periphery, the front portion having a width, the absorbent structure further comprising a pair of opposing lateral flaps connected to the middle portion and folded at least onto the middle portion of the absorbent structure, each of the flaps, when in an unfolded state, extending beyond the outermost lateral periphery, the middle portion having a basis weight where the lateral flaps have been folded that is at least twice the basis weight of the front portion where the flaps are not located, each of the flaps having a width adjacent to the middle portion that is from about 25% to 100% of the width of the middle portion, wherein the absorbent structure defines a length and wherein the pair of opposing lateral flaps extend only a portion of the length of the absorbent structure adjacent to the middle portion.

2. An absorbent article as defined in claim 1, wherein the middle portion is narrower than the front portion and the rear portion.

3. An absorbent article as defined in claim 1, wherein each of the flaps has a width adjacent to the middle portion that is from about 33% to 100% of the width of the middle portion.

4. An absorbent article as defined in claim 1, wherein each of the flaps has a width adjacent to the middle portion that is from about 50% to 100% of the width of the middle portion.

5. An absorbent article as defined in claim 1, wherein the absorbent structure has an hourglass-like shape.

6. An absorbent article as defined in claim 1, wherein each of the flaps is separated from the front portion by a first slit and separated from the rear portion by a second slit.

7. An absorbent article as defined in claim 6, wherein the absorbent structure defines a longitudinal axis that extends from the front portion to the rear portion, the first slits and the second slits being substantially perpendicular to the longitudinal axis.

8. An absorbent article as defined in claim 6, wherein the absorbent structure defines a longitudinal axis that extends from the front portion to the rear portion, the first slits and the second slits extending generally in a diagonal direction in relation to the longitudinal axis.

9. An absorbent article as defined in claim 1, wherein the absorbent structure has a generally uniform basis weight when in an unfolded state.

10. An absorbent article as defined in claim 6, wherein the absorbent structure defines a longitudinal axis that extends from the front portion to the rear portion, the first slits and the second slits extending in a non-linear fashion in relation to the longitudinal axis.

11. An absorbent article as defined in claim 1, wherein the absorbent structure has a non-uniform basis weight when in an unfolded state, the middle portion having a higher basis weight than the front portion and the rear portion.

12. An absorbent article as defined in claim 1, wherein the absorbent structure has a non-uniform basis weight when in an unfolded state, the lateral flaps having a basis weight greater than the middle portion.

13. An absorbent article as defined in claim 1, wherein the absorbent structure has a non-uniform basis weight when in an unfolded state, the middle portion having a basis weight greater than the lateral flaps.

14. An absorbent article as defined in claim 1, wherein the absorbent article is one of diapers, child's training pants, feminine care articles, and incontinence articles.

15. An absorbent article as defined in claim 1, wherein the absorbent structure comprises superabsorbent particles.

16. An absorbent article as defined in claim 1, wherein the absorbent structure comprises pulp fibers and superabsorbent particles.

17. An absorbent article as defined in claim 1, wherein the absorbent structure comprises an air formed web.

18. An absorbent article as defined in claim 1, wherein the absorbent structure has a basis weight of from about 100 gsm to about 2,000 gsm.

19. An absorbent article as defined in claim 1, wherein once each of the lateral flaps have been folded, the middle portion includes areas that have a basis weight that is at least twice the basis weight of the front portion and the rear portion.

20. An absorbent article as defined in claim 1, wherein once each of the lateral flaps have been folded, the middle portion includes areas that have a basis weight that is at least 150% greater than the basis weight of the front portion and the rear portion.

21. An absorbent article as defined in claim 1, wherein once each of the lateral flaps have been folded, the middle portion includes areas that have a basis weight that is at least 3 times the basis weight of the front portion and the rear portion.

22. An absorbent article as defined in claim 1, wherein the front portion includes a center area and two opposing lateral areas and the rear portion also includes a center area and two opposing lateral areas, and wherein, once each of the lateral flaps have been folded, the middle portion, the center area of the front portion, and the center area of the rear portion each have a basis weight that is at least 150% greater than the basis weight of the two opposing lateral areas of the front portion and the two opposing lateral areas of the rear portion.

23. An absorbent article as defined in claim 1, wherein the front portion includes a center area and two opposing lateral areas and the rear portion also includes a center area and two opposing lateral areas, and wherein, once each of the lateral flaps have been folded, the middle portion, the center area of the front portion, and the center area of the rear portion each have a basis weight that is at least twice the basis weight of the two opposing lateral areas of the front portion and the two opposing lateral areas of the rear portion.

24. An absorbent article as defined in claim 22, wherein, once each of the lateral flaps have been folded, the middle portion has a basis weight that is at least 3 times the basis weight of the two opposing lateral areas of the front portion and the two opposing lateral areas of the rear portion, and the center area of the front portion and the center area of the rear portion have a basis weight that is at least twice the basis weight of the two opposing lateral areas of the front portion and the two opposing lateral areas of the rear portion.

25. An absorbent article as defined in claim 1, wherein once each of the lateral flaps have been folded, the middle portion comprises two layers of material.

26. An absorbent article as defined in claim 1, wherein once each of the lateral flaps have been folded, the middle portion comprises three layers of material.

* * * * *